US006498652B1

(12) United States Patent
Varshneya et al.

(10) Patent No.: US 6,498,652 B1
(45) Date of Patent: Dec. 24, 2002

(54) FIBER OPTIC MONITOR USING INTERFEROMETRY FOR DETECTING VITAL SIGNS OF A PATIENT

(76) Inventors: Deepak Varshneya, 3057 Caminito Sagunto, Del Mar, CA (US) 92014-3934; John L. Maida, Jr., 511 Three Corners, Houston, TX (US) 77024

( * ) Notice: Subject to any disclaimer, the term of this patent is extended or adjusted under 35 U.S.C. 154(b) by 0 days.

(21) Appl. No.: 09/499,889

(22) Filed: Feb. 8, 2000

(51) Int. Cl.[7] ............................................... G01B 9/02
(52) U.S. Cl. ..................................................... 356/477
(58) Field of Search ................................ 356/477, 478, 356/479, 481, 483; 250/227.19, 227.27

(56) References Cited

U.S. PATENT DOCUMENTS

| | | | |
|---|---|---|---|
| 4,033,332 A | | 7/1977 | Hardway, Jr. et al. |
| 4,169,462 A | | 10/1979 | Strube |
| 4,634,852 A | * | 1/1987 | Shaw .................... 250/227.19 |
| 5,212,379 A | | 5/1993 | Nafarrate et al. |
| 5,241,300 A | | 8/1993 | Buschmann |
| 5,291,013 A | | 3/1994 | Nafarrate et al. |
| 5,292,013 A | | 3/1994 | Earl |
| 5,295,490 A | | 3/1994 | Dodakian |
| 5,479,932 A | | 1/1996 | Higgins et al. |

OTHER PUBLICATIONS

Withiam–Wilson M.S.N., R.N., Premarket Notification Guide For Breathing Frequency Monitors (Apnea Monitors), Jun. 6, 1988.
Vakoc et al., A Novel Fiber–Optic Sensor Array Based on the Sagnac Interferometer, Journal of Lightwave Technology, Nov. 1999, pp. 2316–2326, vol. 17, No. 11.
Udd, Fiber Optic Sensors Based on the Sagnac Interferometer and Passive Ring Resonator, Fiber Optic Sensors: An Introduction for Engineers and Scientists, 1991, pp. 233–242.
ECRI, Health Devices, Infant Apnea Monitors, Aug.–Sep. 1980.

* cited by examiner

Primary Examiner—Samuel A. Turner
Assistant Examiner—Patrick Connolly

(57) ABSTRACT

A fiber optic monitor that utilizes optical phase interferometry to monitor a patient's vital signs such as respiration, cardiac activity and body's physical movement. The monitor, which is non-invasive, comprises an optical fiber interferometer that includes an optical fiber proximately situated to the patient so that acousto-mechanical signals from the patient are coupled into the optical fiber. Responsive thereto, the interferometer generates a time-varying serial train of fringes which is detected by a photo-detector. A signal processor coupled to the optical detector provides one or more processed output signals indicative of the vital functions. The monitor system has broad applicability, from routine monitoring of infants at home to apnea, arrhythmia and trauma situations. The system can be implemented in embodiments ranging from a low cost in-home monitor for infants to a high end product for in hospital use to monitor infants in nenonatalogy laboratories or at home by physician's prescription. The monitor can be integrated with other sensors such as an EKG, a camera, an oxygen sensor, a carbon-di-oxide sensor, temperature sensor or a microphone to get additional required information depending on the application. When integrated and combined with EKG information, the monitor provides ballisto-mechanical information of the heart for early diagnosis or prediction of cardiac conditions or events. In some embodiments of the monitor, the system can be made portable so that the patient can walk around while still being continuously monitored.

47 Claims, 9 Drawing Sheets

FIBER OPTIC MONITOR USING INTERFEROMETRY FOR DETECTING VITAL SIGNS OF A PATIENT

BACKGROUND OF THE INVENTION

1. Field of the Invention

The present invention generally relates to monitors for detecting cardiac and pulmonary motions such as heartbeat, respiration, physical movement, and other body activities of a patient.

2. Description of Related Art

For detecting vital signs of a patient, there are a number of monitors available with a variety of uses and applications. These vital sign monitors and other advanced monitors range from simple sound monitors such as "baby monitors" used at home, to sophisticated apnea monitors and electro-cardiograms (EKGs) used by physicians and hospitals.

Off-the-shelf low cost, non-prescription baby monitors are currently in wide use to monitor infants at home to verify an infant's well-being. These monitors generally employ a microphone sensor that sends a signal to a remote unit with visual and audio displays. For example, the microphone sensor can be placed close to the crib on a table or hooked up to the crib with a bracket while the remote unit is carried around in the house by parent or other caregiver. Although these units are suitable to monitor low risk infants when they are awake and moving around or crying in the crib, they are not reliable for monitoring them during sleep periods. Parents may be concerned that their child is in jeopardy if they can not hear their child's cries or other normal sounds over the monitor. To address this concern, a parent may make many visits to the room where the infant is asleep to either wait patiently until the infant moves in the crib or attempt to touch the infant in an effort to detect child's breathing.

An alternative system for monitoring infants on the market today uses a rocker switch or pressure/capacitive sensor placed under a mattress to detect the rocking action of the mattress when the infant or other patient moves. To work, such a system requires a hard surface under the mattress and a rocking mechanism placed between the mattress and the hard surface. When the patient moves, the mattress rocks back and forth across a fulcrum causing the sensor to detect the movement. The presence of the right amount of movement might indicate that the patient is healthy, while the lack of movement or too much movement could suggest that the patient is in trouble; although lack of movement does not always reflect that the patient is in trouble. In the case of a small infant who normally does not move much, the sensor may not detect any movement, and accordingly it may produce a large number of false alarms. A significant number of false alarms will undoubtedly cause the parent or caregiver to stop using the device and render it effectively useless. Additionally, the system is not sensitive enough to accurately detect the small-scale acousto-mechanical signals generated by the heart beating, which may provide a complimentary signal that could be used to reduce false alarms.

Neonatologists use apnea monitors for detecting sleep apneic events in premature or high-risk infants, which if not detected can result in Sudden Infant Death Syndrome (SIDS). Generally the apnea monitors are used to detect and measure respiration rate of an infant. In the absence of respiration for about 20 seconds, the monitor sounds an alarm indicating an urgent need for nurse intervention. These type of monitors typically utilize impedance pneumography techniques, in which the electrical sensors are placed on infant's body to detect variations in resistance caused by respiration and physiologic changes when a 10–100 kHz electrical current of about 50 micro amperes is passed through the patient. The voltage developed and measured is proportional to the transthoracic impedance, which varies during each breath. These sensors are designed to measure changes in this resistance, on the order of 0.1–1 ohms for shallow breather infants to normal ones. One problem with these sensors is that they do not provide high enough sensitivity to distinguish between shallow breathing and no breathing. As a result, they generate a large number of false alarms, requiring constant attention of nurses and frequent re-setting of the instrument. To better detect the apneic event, a separate heart rate sensor is often added to apnea monitors. Monitoring the heart rate in conjunction with respiration can lower the false alarm rates because prolonged apnea is frequently followed by bradycardia (i.e. slowing of the heart rate), which is an event that can be measured using the heart rate sensor. Further improvements can be made by incorporating a saturated oxygen monitoring sensor to an apnea monitor. Such a sensor is affixed at the finger tip of the patient using separate electrical leads. Monitoring the changes in oxygen level in conjunction with respiration and heartbeat rates is useful because it can more accurately detect the onset of an apenic event so that appropriate decisions can be made to administer the correct treatment.

Even though addition of both a heart rate sensor and an oxygen sensor to an apnea monitor is useful to reduce false alarms, and better detect apneic events, such monitors still have a number of shortcomings. For example, 1) with the addition of these sensors and associated electronics, the system's cost increases; 2) electrical leads can come loose or break; 3) if the sensors are inadvertently pulled due to body motion or lead tangling, the infant's skin can peel off; 4) the infant's skin can develop dermatitis from electrode creams, gels and adhesives 5) because the sensors are electrical in nature, they are susceptible to interference from electromagnetic sources, static discharge, radio frequencies, and shocks; 6) they do not function properly in the presence of conductive liquids; 7) they utilize a number of sensors and leads to pick up signals from the patients, which can impede the development of mother/infant relationship; 8) unless the respiration sensors are appropriately placed and the controls adjusted properly, the monitor can be sensitive to artifacts generated by heartbeat; 9) patients can not sleep well because they are forced to lie in a certain position determined by the sensors, and cannot move around freely once the sensors and leads are hooked up; 10) if X-rays are required, the sensors must be removed; and 11) the output signals are susceptible to body motion artifacts.

Another type of monitor is a motion sensing/non-impedance type, such as an air mattress that is designed and developed for the detection of sleep apnea. The motion-sensing sensors are based on the principle of air displacement from one segment to another through a manifold, which is measured by a heated thermistor in the manifold. The moving within the mattress air cools the heated thermistor in the manifold, and this temperature change is detected as a breath. Unfortunately, these pads are very sensitive to body motion and vibration artifact, and therefore the respiration signals are not easily detected from the artifacts. In addition, these sensor pads are not rugged enough to fold and flex, and therefore, are difficult to use and store. Furthermore, because the sensor includes an electrically active thermistor, it is prone to electromagnetic interference.

Other monitor types, including sensors with capacitive mattresses, and sensors with magnetic, thermistor, and pressure transducer pads have similar disadvantages. Because most devices used to date are electrical in nature, they have similar shortcomings as described for the impedance or air mattress sensors. None are totally suitable for reliably detecting apneic conditions or near-miss SIDS.

U.S. Pat. No. 5,241,300 discloses a fiber optic breathing sensor that monitors the air movement localized at the nasal cavities. By placing this fiber optic sensor at the base of the nasal cavity, it measures the change in temperature due to air flow. This sensor does not provide the cardiac signal necessary in the clinical diagnosis of the apnea. Although this system may be useful as a supplementary sensor in the detection of central apnea in adults, it cannot be used with infants because it requires a relatively large volume of air displacement for proper operation.

U.S. Pat. Nos. 5,291,013 and 5,212,379 disclose a Fiber Optical Monitor For Detecting Motion Based on Changes in Speckle Patterns. This speckle-based monitor is designed to detect breathing and heart beat when generally a coherent, narrow band light source is launched at one end of a multimode optical fiber. The central part of the fiber is formed into a "blanket" that senses a patient's normal breathing and heart beat motion. The system, using a photo-detector at the other end of the fiber that senses the changes in optical intensity of a 2-dimensional (2D) speckle pattern. The photo-detector's amplitude output signal is related to the integration (averaging) of the number of speckles and its time variation is related to the change or re-distribution in the number of speckles. Using a coherent optical source and a multimode fiber, the speckle-based monitor produces a light cone containing a pattern of varying light intensity at the fiber output generating multiple light and dark grainy spots (a speckle pattern). The speckle-based monitor requires that only a certain fraction of the light cone emitting from the fiber output (i.e. less than all of the emitted light cone) is collected by the photo-detector or two halves of a photo detector. This is necessary because if entire cross-section of the light cone, containing the 2D speckle pattern, is collected by the photo-detector (or two detectors halves), its output will not appreciably change when motion signals such as breathing or heartbeat, are coupled to the fiber.

The 2D speckle pattern is produced primarily due to the multiple intermodal interferences between the propagating spatial modes of the fiber, and interferences caused by the coherent beams mixing on the receiving surface. The pattern produced by the intermodal interference is modulated by the motion signals that are coupled to the fiber, whereas the pattern produced by the receiving surface remains unaffected. The speckle-based fiber monitor thus relies only on the intermodal interferences to detect the motion signals such as breathing and heartbeat.

In the speckle-based monitor, generally a multi-mode fiber is required over a single mode fiber to detect the patient's motion. Without the multi-mode fiber, it is difficult to produce measurable speckle pattern on the optically polished surface of the detector (or two halves) using even a highly coherent light source. This is because specular surfaces can not produce sufficient optical phase shifts required for the coherent light beams to interfere. Single mode fibers do not show intermodal speckle patterns because the interference of the two orthogonal degenerate mode only produces a single light spot, compared to may spots by multi-mode fibers. Higher modes in a single mode fiber may be generated if the operating wavelength of the light source is brought near or below the cut off wavelength of the fiber. These higher order modes may interfere but the speckle visibility is poor due to the presence of only few modes, resulting in poor signal detection and low sensitivity. In addition, the speckle-based monitor requires a coherent light source because incoherent light sources, such as light emitting diodes (LEDs), can not produce a measurable intermodal speckle pattern even if a multimode fiber is used. Therefore, both a coherent light source and a multi-mode optical fiber are needed in the operation of the speckle-based monitor. If compromises are made, the monitor may not be provide sufficient sensitivity to detect and measure patient's motion signals, especially the heart signals.

The speckle-based monitor has a number of shortcomings and limitations. Such limitations can become large disadvantages when design trade-offs are made. For example, the requirement that the light source be coherent and narrow band, limits the laser source choices to gas or distributed feedback (DFB) lasers, which results in high power or high costs requirements. Unfortunately, gas lasers such as Helium-Neon (He—Ne) require high voltages to create the plasma and therefore are not very desirable for use at home or in hospitals where patient safety is paramount. DFB lasers, on the other hand are expensive and therefore less desirable in applications where low cost is important. Less coherent (and less costly) broadband light sources, such as edge light emitting diodes (ELEDs) or laser diodes (LDs) that can be operated at low voltages, are not suitable for speckle-based sensors because they do not generate detectable speckle pattern, with or without a multi-mode optical fiber. Another limitation of the speckle-based monitor is the requirement to place the end of the fiber from the detector at sufficient separation to collect a certain fraction of the speckle cross-sectional area. This requirement affects the detection sensitivity in addition to introducing manufacturing difficulties and correspondingly poor yields. Other limitations of the speckle sensor are: 1) since the fiber is placed as a blanket over the patient, it may not stay over the patient at all times especially when the patient is not attended; 2) in order for the speckle-based monitor to provide adequate sensitivity, it must use multi-mode fibers rather than single mode; and 3) use of simple bandpass or high pass filter designs in the speckle-based monitor are insufficient to reliably extract the heart beat signal from the respiration signal in the presence of body movement. The body's movement can produce noise with frequency components in either signal bands. Since hand, leg or body movements occur typically during apneic events or otherwise, therefore common mode rejection techniques, band pass filters or split detectors can not easily eliminate these unwanted signals.

SUMMARY OF THE INVENTION

To overcome the limitations, shortcomings and disadvantages of prior art, the present invention provides a novel fiber optic monitor that utilizes optical phase interferometry to monitor a patient's vital signs. A number of advantages are provided by using optical phase interferometry for detecting heartbeat, respiration and physical body movement. For example, because these sensors utilize optical phase as compared optical intensity modulation characteristics, they provide a very high detection sensitivity while advantageously needing only single mode fibers. Single mode fibers are widely available, and are much lower in cost compared to multimode fibers. The monitor can be configured with a single sensor and in some embodiments an array of sensors to simultaneously detect physiological parameters such as pulmonary motion, cardiac activity, physical movement, and other body activities in infants, adults, canines, and any other living creature.

Because the system is non-invasive, passive and free from electrical leads, gels and suction cups, it can reliably monitor heart beat and respiration rates in presence of physical movement while remaining virtually transparent to the patient. It has application for the detection of sleep apnea and cardiac disorders in both infants and adults. In addition, it can quantitatively predict the body's physical parameters such as fat/weight ratio, temperature, etc. In some embodiments of the monitor, the system can be made portable so that the patient can walk around while still being continuously monitored. Advantageously, some embodiments of the monitor utilize low cost, broadband sources of optical radiation which are typically safer and more compact providing lower cost, smaller size and weight.

A fiber optic, interferometric monitor for detecting vital functions in a patient comprises an optical fiber interferometer that generates an optical signal responsive to acousto-mechanical signals generated by vital functions of the patient. The interferometer includes optical fiber means for defining two optical paths including a first optical path and a second optical path. The first optical path includes an optical fiber proximately situated to the patient so that the acousto-mechanical signals are coupled to the optical fiber, thereby modulating a physical parameter of the optical fiber responsive to the acousto-mechanical signals. The optical fiber also includes an optical source coupled to supply optical radiation into an input end of the first and second optical paths. The interferometer generates a serial train of fringes from the optical radiation emitted from an output end of the two optical paths. A photo-detector is arranged to sense an optical signal provided by time variations in the fringe train, the photo-detector providing a raw electrical signal responsive thereto. A signal processor is coupled to the optical detector to process the raw electrical signal to provide one or more processed output signals indicative of the vital functions. An output system is provided for communicating the one or more processed signals.

The optical fiber sensor (or a plurality of sensors) is situated in close proximity to a patient, for example a length of optical fiber may be configured into a pad, which can be placed on top of a mattress but under the bed sheet. In such a configuration, the optical fiber sensor (or sensors) is non-invasive, it does not need to be hooked up to a patient using gels or suction cups or leads, and therefore it remains virtually unnoticed by the patient, allowing the patient to rest comfortably.

The monitor system has applicability across a broad spectrum of fields, from routine monitoring of infants at home to apnea, and arrhythmia that occur in sleep labs, emergency rooms, operating rooms intensive care units (ICU) and rescue and ambulatory vehicles. The system can be implemented in a wide variety of embodiments ranging from a low cost in-home baby monitor to a high end apnea monitor for in hospital use to monitor infants in nenonatology laboratories or at home by physician's prescription. The monitor can be used for providing additional and complimentary ballisto-mechanical information to be combined with EKG information for early diagnosis or prediction of cardiac conditions or events. If it is used to monitor respiratory rate, an increase may indicate acidotic condition as might be seen with septic shock or diabetic ketoacidosis. The monitor may also be used for monitoring adults in convalescent homes for the detection of vital signs or in psychiatric wards to detect presence of patients in bed. For military applications, the monitor may be used to monitor physiological and pathological changes in personnel under various combat or training conditions as well as in trauma facilities.

BRIEF DESCRIPTION OF THE DRAWINGS

For a more complete understanding of this invention, reference is now made to the following detailed description of the embodiments as illustrated in the accompanying drawing, wherein.

DETAILED DESCRIPTION

Figure 1:
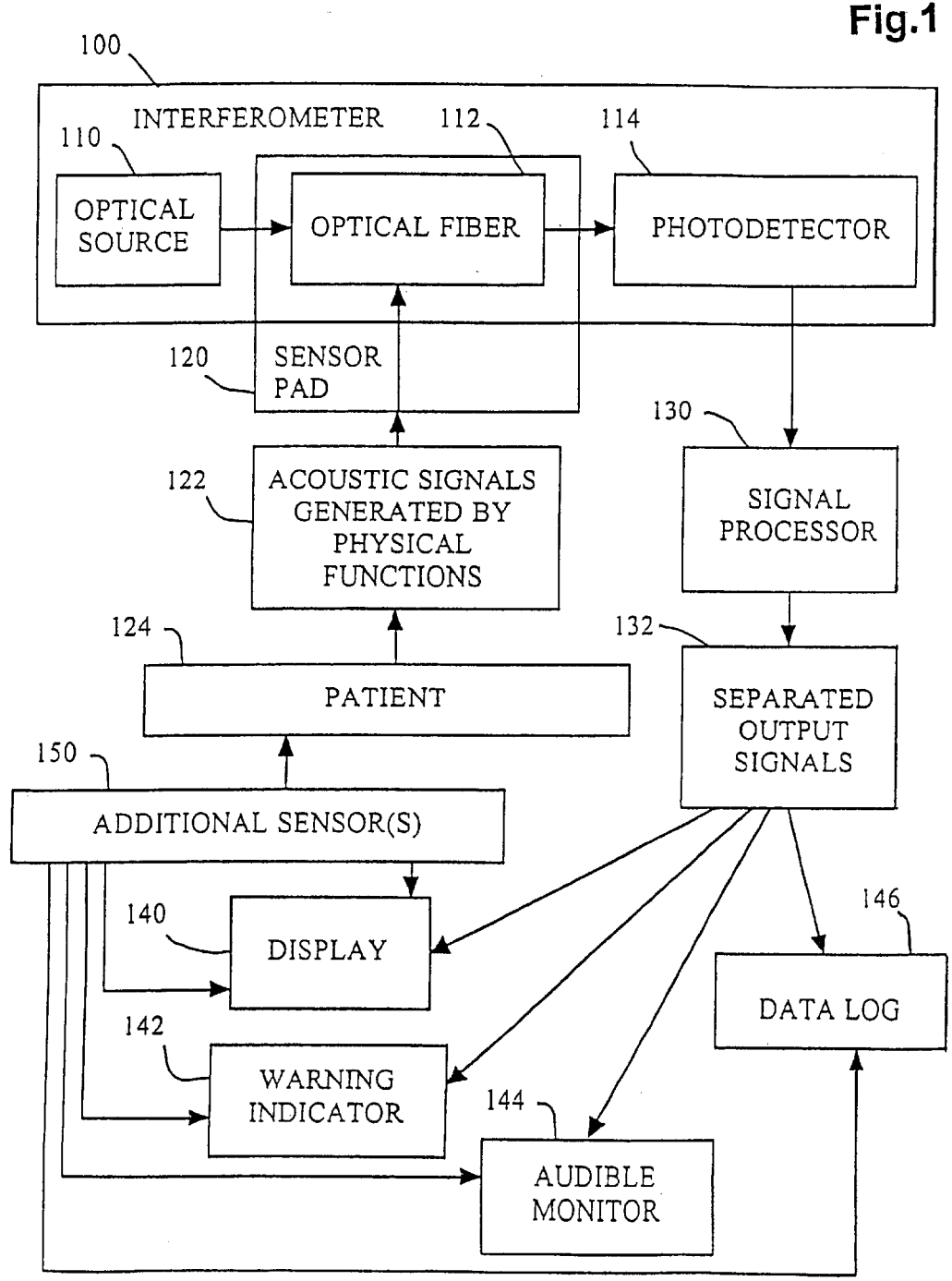
FIG. 1 is a block diagram illustrating an interferometric fiber optic monitor for detecting heartbeat, respiration, and physical movement in a patient.

This invention is described in the following description with reference to the Figures, in which like numbers represent the same or similar elements.

As used herein, the term "patient" is used in its broadest sense to include any living creature that has vital functions or other activities that generate characteristic acousto-mechanical signals. Although the monitor may be described herein in terms of its applicability to humans, it also may be applied to canines or any other type of animal.

A. Overview

A non-invasive, non-intrusive fiber optic-based monitoring system is disclosed that uses interferometry to measure acousto-mechanical signals such as heart rate, breathing rate, and physical movement without electrical wires, cables, tubes or anything else 'hooked up' to the patient or animal. The patient simply sits, lays down on the sensor pad, or wears it as a garment, and the acousto-mechanical signals from the heart beating, breathing (expansion or contraction of chest cavity) or physical movement are measured as minute (micro inch) changes in pressure on the fiber optic interferometer sensor pad. The detected acousto-mechanical signals are processed to separate the heart beat, breathing, and physical movement signals. The separated signals are then communicated by means such as displays that visually present the signal as actual numbers, flashing indicators, audio tones, or alarm functions if vital signs exceed the preset levels or cease entirely.

The system includes an optical fiber-based interferometer sensor situated proximate to a patient. The interferometer senses vital function signals such as the acousto-mechanical signals generated by the patient. Specifically, vital functions such as cardiac activity, respiration, and movement generate characteristic acousto-mechanical waves that are transmitted through the patient's body to the optical fiber proximately situated to the patient. Advantageously, the fiber optic-based vital sign monitoring system non-invasively and non-intrusively measures the "ballisto-mechanical" response of the patient's cardiac system, the pulmonary system and physical movement.

More particularly, the optical fiber-based interferometric monitor utilizes optical phase measurement techniques to sense the acousto-mechanical signature generated by the body's vital functions. The optical fiber is energized using an optical source and the acousto-mechanical signals generated by the body modulate the light signals, in the form of a serial/train of fringes (series of single light spots). These time varying fringes are emitted from the optical fiber and are detected and processed using a photo diode, amplifier and electronics. In one embodiment, the optical fiber is incorporated into a sensor pad, and the optical source and the photo-diode along with the processing electronics are packaged in an assembly (an electro-optic unit) placed close to the sensor pad. When acousto-mechanical pulses propagate in the fiber sensor pad, the length of the fiber changes microscopically (on the order of the wavelength of light) corresponding to the amplitude of acousto-mechanical signal and its characteristic frequency spectrum. The change in fiber length changes the optical path length of the light mode propagating in the fiber. This change in the optical path length is directly related to the optical phase change of the unperturbed light mode which is modulated by the acousto-mechanical signal. When the modulated optical light mode, is allowed to interfere with the unmodulated optical light mode, at the photo-detector or power coupler/splitter, a serial train of optical fringes (i.e. a time-varying series of light-dark-light-dark etc. outputs) is generated that changes according to the temporal characteristic of the acousto-mechanical signal. Although the term "fringe" is used herein in accordance with conventional usage, the optical fringes typically appear without a discernible fringe pattern, evidenced by only by a cone whose intensity varies between light and dark. By detecting this serial train of fringes as a function of time, the applied acousto-mechanical signal is retrieved. When the convoluted optical signal is processed further, the three intrinsic signals are separated using digital signal processing (DSP) or other electronic circuit techniques and displayed on a monitor or recorder depending upon the application.

Fiber optic technology is widely used for many purposes such as communications and remote sensing of physical processes. Fiber optic-based sensors have many advantages. For example, they are light weight, rugged and corrosion-resistant. Furthermore, optical signals transmitted through optical fibers are immune to electrical or magnetic interference. Also, because optical fibers are corrosion-resistant, the sensors can be easily sterilized, which is important for medical uses and because optical fibers are passive, the threats of patient electrocution and data corruption that exits with other monitors are eliminated. These advantages and others make a fiber optic-based monitor useful in a variety of environments, such as for example monitoring the vital signs of infants and adults in home, in-hospital and in military situations. When configured properly, a fiber optic-based monitor can also be used to quantitatively predict body's physical parameters such as fat/weight ratio temperature by comparison of the transmitted heart signals with varying body fat content.

Monitoring both the cardiac and pulmonary responses is important in the prediction and diagnosis of cardiac disorders and/or apenic conditions. Monitoring the patient utilizing a conventional EKG, where an electrical instruction is generated at the heart and regulated by signals from the brain, can provide the patient's cardiac rhythm. However, a good EKG signal does not necessarily guarantee that the heart has produced a good mechanical response during that particular EKG signal. Nor does a train of equal shape EKG signals assure that there was a concomitant train of equal mechanical or ballistic responses. Researchers believe that by exploiting heart's ballistic information in addition to pulmonary information (respiration rate and saturation) may be a key to discovering new ways to investigate and understand the pathological/physiological changes apart from the usual cardiac rhythm generated by existing EKG cardiac monitors and pneumographic pulmonary devices. Subsequently, this ballistic information in conjunction with EKG can be used in the diagnosis of cardiac disorders such as atrial/ventricular fibrillation (arrhythmia), which is a leading cause of death in adults. The fiber optic sensor system disclosed herein can provide the ballistic response of heart, and therefore could be a very useful instrument when used with an EKG. If the system is configured to detect abdominal vs. chest movements, it could be useful to diagnose and detect more accurately pulmonary disorders such as obstructive apnea, which is suspected as a leading cause of death in infants. Therefore it is believed that such a system can be used in conjunction with an EKG and other sensors, and may be useful in wide variety of medical applications ranging from simple monitoring of vital signs to more complex detection, diagnosis and prediction of various medical conditions including atrial fibrillation and obstructive apnea.

In one embodiment, a low cost fiber optic-monitor can be used at home, replacing the commonly-used sound monitors that are inadequate especially during sleep periods. The low-cost embodiment can be designed to detect three signals (cardiac, pulmonary, and physical movement) and generate an alarm in the absence of an individual signal or any combination thereof. The three signals may be transmitted wirelessly to a remote unit. A microphone sensor may be added to the monitor to detect and transmit the normal sounds of the infant to this remote unit and/or a camera may be added also. The remote unit is carried around in the house by the parent or other caregiver. The three signals as well as the normal sounds and video image may be displayed in different ways on the remote unit, which is described in more detail elsewhere herein.

In another embodiment, the system can be configured to reliably measure and separate the same three signals even during the presence of body's physical movement, which otherwise would dominate and "wash out" the other two signals. Reliable separation and identification of the signals (cardiac, pulmonary, and physical movement) substantially reduces the false alarm rate by combining information from each of the three separated signals. Such a system may be used in applications varying from apnea detection in high-risk infants to atrial/ventricular fibrillation detection in adults under physician's care. Separation of the signals using various signal processing techniques is described elsewhere herein.

B. Description

Reference is now made to FIG. 1, which is a block diagram illustrating an interferometric, fiber optic monitor. An interferometer 100 includes an optical source 110, an optical fiber 112, and a photo-detector 114. At least a portion of the optical fiber 112 is incorporated into a sensor pad 120 that is situated to receive acousto-mechanical signals 122 generated by a patient 124. In the interferometer, light from an optical source 110 is launched into an optical fiber 112, and the light is modulated within the optical fiber by the acousto-mechanical signals 122. In response, the interferometer generates a time-varying serial train of fringes which are detected by the photo-detector 114 producing an electrical signal responsive thereto. The electrical signals generated by the photo-detector are supplied to a signal processor 130, such as a digital signal processor (DSP) that separates the signals as indicated at 132. The separated signals are then utilized as desired. For example, the signals may be supplied to a display 140, a warning indicator 142, an audible monitor 144, and/or a data logging device 146.

The interferometer 100 can be implemented in many different configurations. For example, a Fabry-Perot interferometer, a Mach-Zehnder interferometer, a Sagnac interferometer, or a Michelson interferometer may be used. Many interferometer configurations are known, some of which are described elsewhere herein. Generally, an interferometer provides at least two different optical paths. The light from the optical source is divided between the two optical paths, and the photo-detector detects the phase difference or other characteristics of the fringe train created at the far (distal) end of the two optical paths. The acousto-mechanical signals 122 change (modulate) one of the optical paths but not the other (or not the same amount), thereby creating a serial train of time varying (modulated) fringes responsive to the acousto-mechanical signals. Some interferometers, such as a Mach-Zehnder interferometer, utilize two optical fibers to provide the two different optical paths, while other interferometers such as a Sagnac interferometer utilize a single optical fiber into which light from the optical source is injected simultaneously into both ends using a fiber splitter/coupler. Accordingly, the interferometer 110 may comprise a single optical fiber or it may comprise two optical fibers to provide the two different optical paths.

Generally, the optical source 110 comprises any suitable source of light, such as an edge emitting diode (ELED), a light emitting diode (LED), a semiconductor laser diode (LD) similar to those used to read conventional CDs, or a gas laser tube. The optical source is chosen to be suitable for the implemented type of fiber interferometer. For example, a Sagnac interferometer can utilize a low cost ELED while a Mach Zehnder interferometer requires a laser diode of suitable coherence length. Likewise, a Fabry-Perot interferometer may require more highly coherent light sources such as a He—Ne or a DFB semiconductor laser, which is compact in size but expensive compared to a He—Ne laser.

Light is coupled from the optical source 110 into the optical fiber 112 using any suitable means such as direct coupling or an imaging lens. Beam shaping devices may be utilized to shape the beam for more efficient coupling. Utilizing the imaging lens allows about a 10 dB improvement in the signal that is launched into the fiber. In order to further reduce losses, a optical matching index gel may be inserted between all glass-air-glass interfaces. Use of index-matching gel makes the glass fiber interface nearly transparent, which substantially reduces unwanted reflections and optical noise generated from these interfaces. Unwanted reflections are produced from glass-air-glass interfaces by the Fabry-Perot cavity modes if no gels are used.

The optical fiber 112 comprises any suitable fiber, for example it may be a single-mode, multi-mode step index fiber, or a graded index fiber. Generally, the type of fiber is determined by the type of interferometer and other design considerations. The choice of optical fiber is described in detail elsewhere herein.

The photo-detector 114 detects the serial train of optical fringes at the far end of the optical paths in a conventional manner and converts them into equivalent electrical signals. In one embodiment, the optical fiber is butted against the glass window of a single photo-detector that has an active area large enough to accept the cone of light emanating from the fiber or directly to the chip with the glass window removed. The detector may be mounted using a SMA, FC, ST connector or other connector configurations or in a non-connectorized housing.

The sensor pad 120 positions at least part of the length of the optical fiber 112 proximate to the patient 124, where it can receive the acousto-mechanical signals 122. Several embodiments of the sensor pad will be discussed, and many others are possible.

Figure 11:
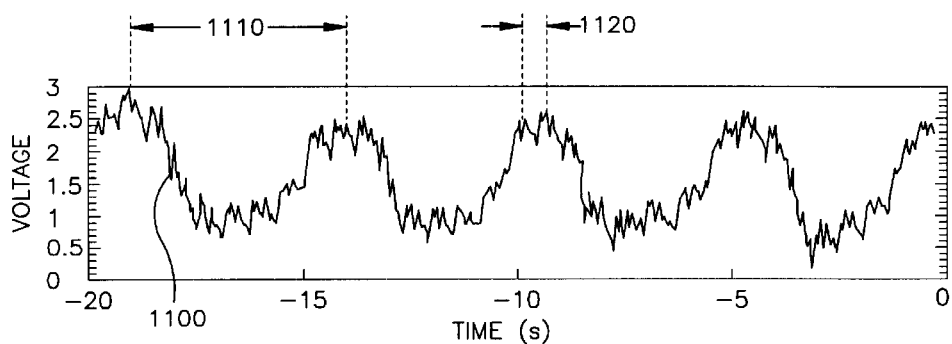
FIG. 11 is a graph of amplitude vs. time, showing experimental data in one embodiment in which heartbeat and respiration of a normal infant are output in the form of a combined signal.
Figure 12:
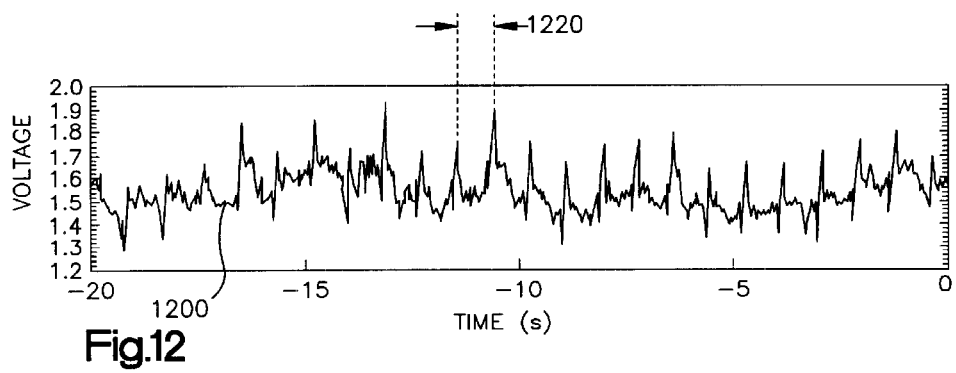
FIG. 12 is a second graph of amplitude vs. time, showing experimental data in a second embodiment in which heartbeat and respiration of a normal infant are output in the form of a combined signal.

The signal processor 130 comprises a circuit that receives the raw electrical signal from the photo-detector and processes it into separated signals 132, which are suitable for the particular embodiment. As previously discussed, the photo-detector detects the periodic intensity changes of the optical fringe serial train over time, and generates a raw electrical signal responsive thereto. The amplitude of the raw electrical signal varies in time in accordance with the frequency response of the acousto-mechanical modulation. The raw electrical signal is further processed by the signal processor 130 to provide one or more output signals. The design of the signal processor 130 and its separated signals 132 are dependent upon a number of factors such as the information desired (e.g., heartbeat, respiration, and/or movement), the desired accuracy of the data, and the type of interferometer chosen for the embodiment. For example, a simple analog circuit design for a signal processor may include a low-pass filter and a high-pass filter to separate the heart and breathing signals from movement-related signals. In one such an embodiment, such as described with reference to FIGS. 9A and 9B, the low-pass filter outputs a signal that combines heart-rate and breathing signal in one combined signal that can be displayed on a single screen. Because the heartbeat signal typically has higher fringe train rate or frequency than the respiration signal, the combined signal can be displayed in the form of the higher-frequency heartbeat superimposed upon the lower-frequency breathing such as shown in FIGS. 11 and 12.

Another example of a signal processor 130 is a digital signal processor that converts the raw electrical signal into a digital signal and then processes it using digital signal processing techniques to separate the signals into three of more components such as heartbeat, respiration, and physical movement. Such signal processors can be highly sensitive, and can be implemented in a number of ways, such as a programmed microprocessor, a dedicated ASIC (Application-Specific Integrated Circuit) and/or a computer. Digital signal processing techniques such as autocorrelation, fast Fourier transforms, and/or pattern recognition coding may be used. Furthermore, sophisticated processing techniques may be used, such as artificial intelligence-based programs may be trained to recognize the pattern of particular events of interest, such as an impending apneic event, or an impending heart attack, and provide a warning signal responsive thereto. Such a signal can be particularly useful to quickly trigger an alarm if the recognized event is life-threatening, such as an impending heart attack in an adult, or an impending SIDS event in an infant. If the recognized event is less important, it may simply be recorded.

The separated signals 132 are then transmitted via a suitable interface to an appropriate output device, such as the display 140, warning indicator 142, audible monitor 144, and/or data logger 146. In some embodiments the separated signals 132 may be communicated by a wire connection. Alternatively or in addition thereto, a suitable wireless communication system may be used to transmit the separated signals 132 from the signal processor to any of the output devices.

In some embodiments, additional sensors 150 may be utilized to monitor physical parameters of the patient in conjunction with the fiber optic interferometer. Examples of these additional sensors include a microphone, a camera, an oxygen sensor, a carbon dioxide sensor, an EKG system, and a second (or plurality of) fiber optic interferometer(s).

Figure 2:
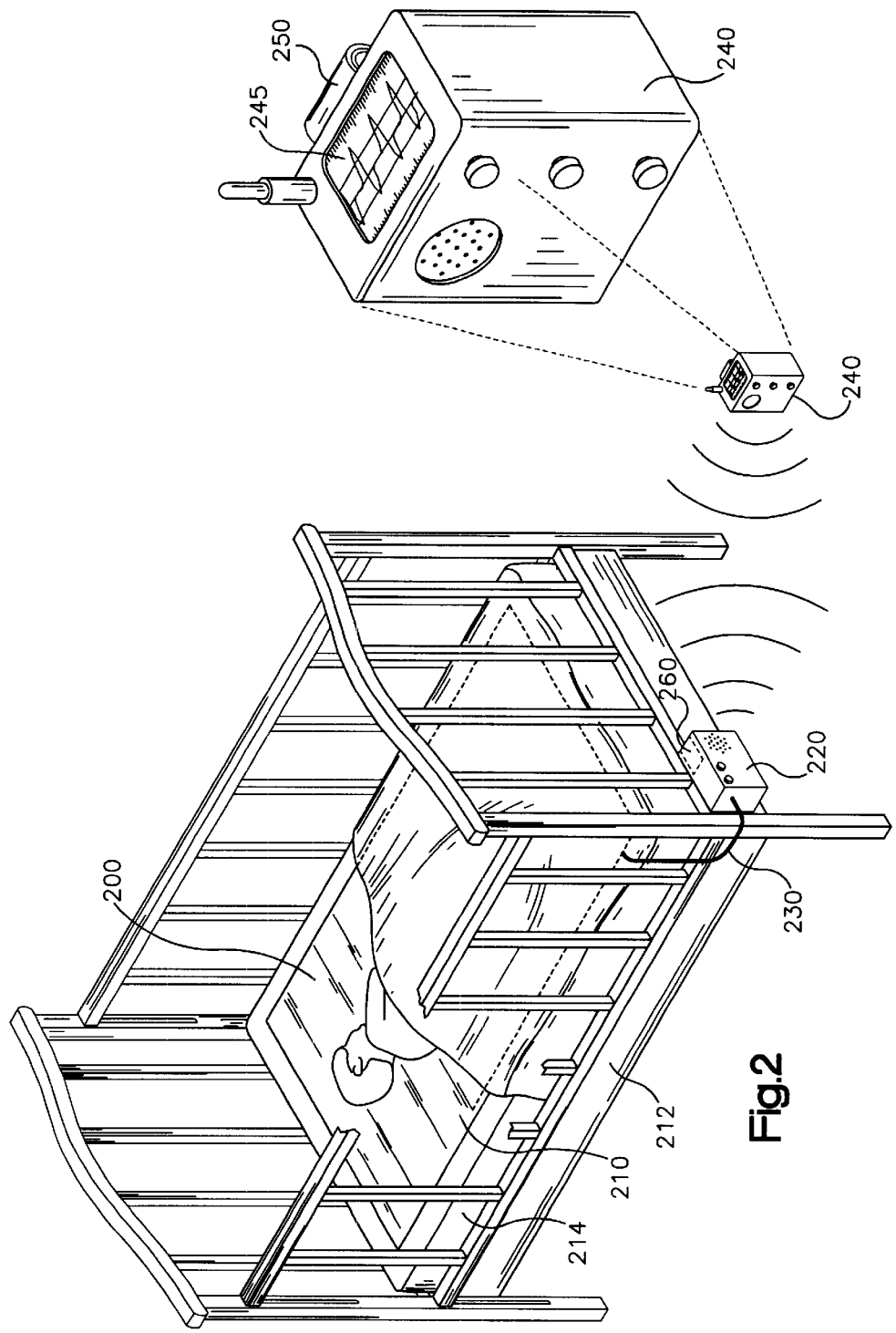
FIG. 2 is perspective view of an embodiment of a fiber optic sensor for detecting the heartbeat, respiration, and physical movement of an infant in a crib, including a portable device for remotely monitoring the infant.

Reference is now made to FIG. 2, which is a perspective view of an embodiment of a fiber optic sensor for detecting the heartbeat, respiration, and movement of an infant 200. In this embodiment, the sensor pad has a rectangular configuration 210 designed to fit into a crib 212, and the optical fiber situated within the sensor pad is generally configured in a pattern from side to side along the entire length of the pad. The sensor pad is placed on top of a mattress 214 and optionally under the bed sheets. The infant lies on the sensor pad, which effectively couples the acousto-mechanical signals generated by the infant's vital signs into the optical fiber within the sensor pad. Advantageously, the sensor pad is not hooked up to the infant directly, which allows the infant to shift his/her position within the crib while still being monitored. An electro-optic unit 220 affixed to the crib houses the optical source, photo-detector, signal processor, and other circuitry. The sensor pad is coupled by an optical fiber interconnect 230 to the electro-optic unit. The separated signals are transmitted via a transmitter such as a RF transmitter in the electro-optic unit to a remote receiver such as the portable unit 240 that displays heartbeat and/or respiration on an LCD display 245. The battery-operated receiver can be carried by a parent, doctor, nurse, or other individual, and in some embodiments includes a system for generating audible or visual warning signals responsive to predefined conditions, such as reduced heartbeat or cessation of breathing for more than a preset time. The embodiment illustrated in FIG. 2 includes a belt clip 250 for easy portability. The portable unit can be used in conjunction with a desktop unit (not shown in FIG. 2) that could be placed on a night stand or in the vicinity of the guardian, parent, or caregiver.

In order to ensure the integrity of the communication link between the electro-optic unit and the remote unit, a fail-safe communication may be used, such as a handshaking routine implemented in the two units by using a two-way RF link and also provide an input for an alarm condition. The electro-optic unit and/or the remote receiver can also provide a blinking LED, an LED array or an LCD responsive to the heart rate and breathing for the monitored infant. In the case of an alarm condition, such as the absence of heart rate, or breathing, or movement, the alarm will be activated. Many different alarm types are possible, for example, a beeper, a voice response unit, or a vibrator may be actuated to alert the guardian, parent or caregiver that a serious condition exists.

In addition to the fiber-optic based sensor, some embodiments may utilize an additional audio system, such as a microphone sensor 260 connected along with an RF transmitter, both of which are located in the electro-optic (e-o) unit in the embodiment shown in FIG. 2. The microphone may be integral to the e-o unit, as shown, or may have another form, such as integrated within the pad itself. The microphone 260 detects the normal sounds of the infant and transmits them wirelessly to a remote unit 240. Such a configuration, in which the microphone sensor simultaneously monitors the infant's sounds described herein, can be useful to provide higher confidence to the parent or other caregiver especially during periods when the infant is awake and moving around in the crib.

Figure 3:
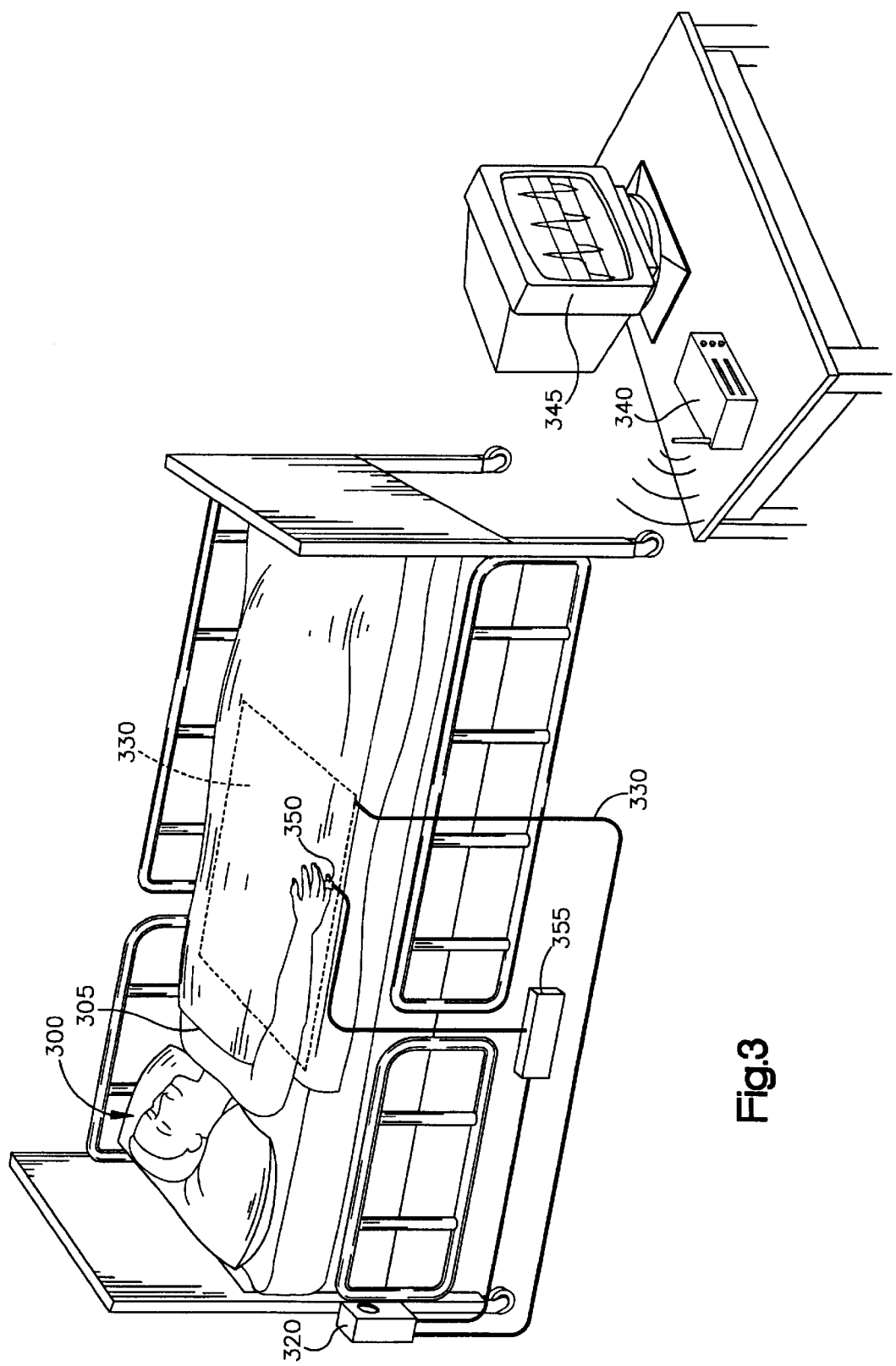
FIG. 3 is a perspective view of an embodiment of a fiber optic monitor for detecting the heartbeat, respiration, and physical movement of a patient confined to a hospital bed.

Reference is now made to FIG. 3, which is a perspective view of an embodiment of a fiber optic sensor for detecting the heartbeat, respiration, and movement of a patient 300 confined to a hospital bed 305. In this embodiment, the sensor pad has a rectangular configuration 310 shown by dotted lines designed to fit under the section of the patient's body near to the heart and lungs. The sensor pad is placed on top of a mattress 312 and optionally under the bed sheets and the optical fiber situated within the sensor pad is configured generally in a zigzag pattern from side to side along the entire length of the pad. The patient lies on the sensor pad, which effectively couples the acousto-mechanical signals generated by the patient's vital signs into the optical fiber within the sensor pad. Unlike other monitors, the sensor pad is not hooked up to the patient directly, which allows the patient to shift his/her position within the bed while still being monitored. An electro-optic unit 320 affixed to the bed houses the optical source, photo-detector, signal processor, and other circuitry. The sensor pad is coupled by an optical fiber interconnect 330 to the electro-optic unit. The separated signals are transmitted by any suitable means, such as a radio signal or a cable, to a remote receiver 340 that displays heartbeat and/or respiration on a CRT monitor 345. The receiver can be situated in a nurse's station, for example. The receiver may also include a system for generating audible or visual warning signals responsive to predefined conditions, such as reduced heartbeat or cessation of breathing for more than a preset of time.

In addition to the fiber-optic sensor, some embodiments may utilize an additional sensor, such as an oxygen sensor 350 that is affixed to the patient's finger to detect the levels of saturated oxygen or carbon dioxide in the patient. The oxygen sensor 350 is connected to a suitable monitoring unit 355, which may in turn be connected to the electro-optic unit 320. Such a configuration, in which the finger-situated sensor simultaneously monitors the patient with the fiber optic monitor described herein, can be useful to more accurately detect apneic events. Additional sensors can be utilized in other embodiments to include an EKG, either alone or in combination with the oxygen sensor.

In some embodiments, the sensor pad 310 and the electro-optic unit 320 include two or more fiber optic interferometers so that two or more separate optical fibers are situated to receive acousto-mechanical information from the patient. The multiple fiber optic interferometers can be utilized for a variety of reasons, such as to provide greater accuracy and sensitivity and in some cases to detect obstructive apnea.

Figure 4:
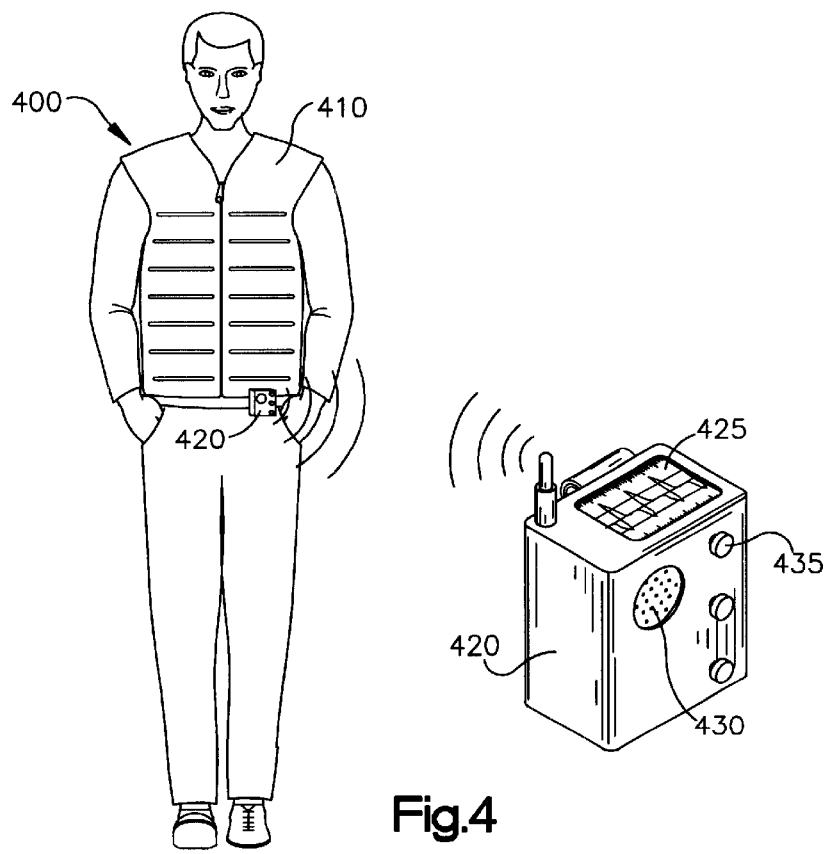
FIG. 4 is a perspective view of an embodiment of a fiber optic monitor for detecting the heartbeat, respiration, and physical movement of an ambulatory patient.

Reference is now made to FIG. 4, which is a perspective view of an embodiment of a fiber-based sensor for detecting the heartbeat, respiration, and movement of an ambulatory patient 400. In this embodiment, the sensor pad is configured or stitched into a garment 410 that is designed to be worn like a vest, which advantageously allows the person to be mobile and not constrained to bed. The garment has a configuration that situates the embedded optical fiber in close enough proximity to the patient's body to couple acousto-mechanical waves into the optical fiber. The sensor pad in the garment is coupled by an optical fiber interconnect to an electro-optic unit 420. The electro-optic unit 420 is carried by the patient, and houses an optical source, a photo-detector, a signal processor, and other circuitry. The electro-optic unit may comprise a visible display such as an LCD monitor view able by the patient, and may also include a system for generating audible or visual warning signals responsive to predefined conditions such as speaker 430 and an LED or LED array 435. In alternative embodiments, the signals from the electro-optic unit may be transmitted by any suitable means, such as a radio signal or a cable, to a remote receiver such as in a nurse's station or other centralized location.

Advantageously, the sensor pad can be made of materials that are relatively soft, water proof/resistant and comfortable, which is particularly useful in the garment configuration shown in FIG. 4 as well as in the mattress configurations of FIGS. 2 and 3. Another advantage is that the optical fiber and sensor pad can be rolled and stored without damaging the embedded optical fiber. The size of pad can be made to fit a crib, or a full size bed. In operation, the pad can be either placed on a mattress (infant/adult), under the bed sheet and secured using elastic bands and/or Velcro at each corner, or stitched into a patient's garments. Thus, the sensor pad remains substantially invisible to the patient, reducing physical damage and avoiding negative psychological effects.

C. Optical Fiber Sensor Design

To design a sensor pad as described herein that uses optical phase interferometry to detect the vital signs of the human body or canines, it is useful to determine the optical fiber sensor length required to adequately detect the acousto-mechanical pressure generated by the heart beat or respiration By limiting the serial train of fringes swept over a unit time to about 500–1000 fringes, it is found empirically that a minimum fiber sensor length of about 10 meters is adequate to detect heart and respiration signals of both infants and adults. Nevertheless, longer fiber lengths can improve the detection sensitivity because of the increased sensing area under the patient for the same acousto-mechanical signal. But by trading off the number of fringes detected per unit time against the fiber length and the pad area for a given acousto-mechanical pressure, the sensor designed may be optimized for a specific application.

Optical Fiber Embodiments

In designing a sensor pad using an optical fiber, several factors must be considered, such as minimizing optical attenuation in bends (macroscopic as well as microscopic), ensuring the fiber is mechanically rugged so that it does not fail when bent, and efficiently coupling of the fiber to the optical source.

Although many types of optical fibers can be used, two different embodiments of optical fibers are of particular interest: a single mode step index fiber and multi-mode graded index fiber. Both optical fibers are made from fused silica glass, have excellent optical and mechanical properties, and produce minimum optical attenuation in tight bends. In one embodiment the single mode fiber is 7/125/250/900, for example. In another embodiment the multi-mode graded index fiber is 62.5/125/250/900, for example. The 250 micron diameter buffer is a UV acrylate and 900 micron is made from an elastomeric polyester. Suitable optical fibers are manufactured by Corning Glass of Corning, N.Y.

Both fibers have excellent mechanical properties when subjected to bends. Mechanically, the fiber should not fail when subjected to bends in the pad. Because the minimum bend radius of this particular fiber is approximately 0.25 inch, it is adequate for use in a pad configuration, which has bends much greater than 0.25 inch., If the bend radius used in the pad is 0.825 inches, the bend stress can be calculated as 31.5 kpsi based on the relationship that $S=Er/R$. This bend stress is three times less than the proof strength, which warrants a fiber life greater than 30 years and approaching 40 years using the fatigue resistance parameter of about 20. This is in agreement with the measurements provided by a leading manufacturer, Spectra-Corning, Avon, Conn., where the stress level required for a forty year life is about 34.5 kpsi using n=20. However, for fibers with n=30, such as Corning's Titan (titanium doped) single mode fiber, the bend radius can be small as 0.52 inch for a 40 year lifetime. Fibers with 80 microns OD compared to 125 can have even smaller bend radii and still maintain a 40 year life expectancy.

In one embodiment, the sensor pad fiber life expectancy at bend radius of 0.825 inch is better than 30 years. Additionally, since this fiber is proof tested to 100 kpsi at the factory, freak fiber failures are screened. The fiber life and strength can be improved further by utilizing surface clad coatings such as titanium-doped silica, hermetic diamond-like coatings and/or hard polymeric coatings.

The sensor fiber required must exhibit low optical losses due to bending. The excess loss in the fiber is less than 1 dB from the first five 0.5 inch diameter bends and almost no loss beyond that. As is known to those skilled in the art, to minimize optical bend losses it is desirable to use a large numerical aperture (NA) fiber. Large NA fibers are less susceptible to macro bending/micro bending losses as they can contain the light even at large bend angles minimizing the leakage of light from the core to clad and into the buffer. In this case, the graded index fiber had an NA=0.27, whereas for the single mode the has the NA of about 0.1. It was observed that when a patient rested on the pad, no significant loss could be measured. However, the system is designed to operate with optical losses of approximately 20 dB, of which 2–3 dB could be due to body weight.

The single mode fiber was evaluated to further investigate the possibility of enhancing the fringe visibility while reducing signal fading. The single mode fiber can provide improved interferometric sensor performance over a multi-mode design because of the absence of signal mixing and/or coherent superposition summing between adjacent spatially transverse wave guide modes. Therefore the signal mixing and subsequent signal fading is substantially reduced although not completely eliminated. It is believed that if a polarization preserving single mode fiber wave guide is used, the signal fading can be essentially eliminated. However, because of the high cost of the polarization preserving fiber, one compromise is to use a short section of the polarization preserving fiber along with the single mode fiber.

Either single mode fiber or multimode fiber can be used depending on tradeoffs associated with the interferometer type chosen, the sensitivity desired and the design cost goals. For example, multi-mode fibers can be easily coupled to a diode source requiring less touch labor compared to coupling single mode fibers that require careful design considerations to optimize the optical throughput. However, when trading off performance, the single mode fibers provide much better fringe visibility (sensitivity) compared to that achieved using multi-mode fibers.

Sensor Pad Embodiments

Although for the reliable detection of both heart and respiration signals in infants and adults, many configurations of the sensor pad are possible, only two are discussed below. There are four basic design principles implemented in the design of the fiber optic pads. First, it should be mechanically rugged so the optical fiber embedded in it does not break when folded, flexed, cleaned or due to body weight/movements. Second, it should not produce safety hazards. Third, the fiber should stay in place and cover the entire area of the pad so that the patient may move around freely without any restrictions. Fourth, the manufacturing design of both the optical fiber sensor pad and the interconnect should be cost effective.

In a first sensor pad embodiment, the optical fiber is stitched on a fabric substrate and encapsulated in a soft but durable plastic casing/shell for protection. The casing resembles a pillow cover-like configuration, with three sides closed and the fourth side open. To allow the fiber-sensor pad to conform to the contour of the human body, optimize mechanical displacement for respiration detection and achieve good coupling to detect heart signals, an appropriate size foam rubber sheet was added on the underside of the substrate before encapsulation. After encapsulating the fiber stitched substrate and the foam sheet into the casing, the fourth side of the casing is closed using conventional stitching. Alternatively, his step may be done using heat sealing at the edges. The fiber is allowed to exit on one corner of the substrate after it is strain relieved into the substrate along with the inter-connect tubing.

A typical heavyweight fabric can be chosen as the substrate on which the fiber is integrated. The fabric is cut to size for a typical rectangular crib and the edges of the fabric are stitched together. Following this procedure, a number of piping channels (0.5 inch wide by 18 inch length) are made from the same material, then cut to size and stitched into the substrate separated from each other by 1.75 inches. These channels were sewn normal to the length of the fabric. In this configuration, seventeen optical fiber channels were created to allow the fiber to zigzag through the channels for the entire length of the substrate. The channels in this sample are stitched to the substrate such that they will provide sensor coverage for the full length of the patient's body. The piping channels are left open at the ends for threading the optical fiber from one channel into the next. The optical fiber was then threaded through these channels and the exposed U-shaped configuration of the fibers each end are subsequently covered and stitched into place. The fiber sewn fabric substrate is then slipped into the pre-fabricated casing. The fourth side of the casing is temporarily closed and the ingress and egress of the fiber to the casing is confined to one corner of the casing where it is strain relieved. Accidental bending and flexing of the optical in a radius less than 0.25" is restricted by the use of foam placed under the substrate.

The casing is made from a quilted plastic material that is designed lone area larger than the substrate to allow easy insertion into the substrate. This material is quite rugged, water-resistant and fire retardant. After cutting two sheets of material to size, the sheets are conventionally stitched together at three sides and the fourth side is left open for sensor substrate insertion. Such a pad configuration may be further enhanced for improved signal coupling from young infants with body weights so low that the pad does not flex enough to get good signal coupling. Enhancement may be achieved by affixing the fiber sensor pad across a frame of appropriate thickness and size suspending the pad above the surface, leaving an air gap between the pad and the surface. This configuration allows the infant to flex the pad in the air gap, thereby providing better signal coupling.

In a second sensor pad embodiment, the same heavy weight fabric for integrating the optical fiber is used as in the first embodiment. However, the difference in the second design is that the pad size is made much smaller and two straps are added on the sides of the pad. One purpose of the straps is for better detecting the chest and abdomen breathing of the patient and to better secure the pad on the patient. In addition, the material used to cover the sensor substrate is different, because the pad is worn as a garment where factors such as comfort, feel and fit are given more importance. The under side material of the straps is carefully selected also to ensure that the straps do not slip when locked in place on the body. This material is silicone based and is stitched in to the straps. The width of the straps is about one inch while the length is adjustable.

The optical fiber is stitched into the pre-cut substrate using the previously described piping channel approach. The piping channels are stitched into the substrate in such a way that the fiber enters the substrate in the middle, makes a 120 degree turn and then goes down the length of the strap. At the end of the strap, the fiber makes a U-turn and then goes into the other strap of the same set. After making a turn in this strap, the fiber is routed into the pad area where it is serpentine and then routed through the next set of straps similar to the first one. It is important that the fiber routing between a set of straps is continuous to ensure that the breathing induced strain is directly coupled into the fiber and while the heart pressure pulses are coupled in it.

Sensor Pad Manufacturing Design Embodiments

The fiber sensor pad or the integrated garment may be manufactured using the conventional molding and sealing approaches. In a mold having fingers spaced appropriately, a material of right compliance and compressibility such as high density foam is positioned. Optical fiber is then strung in a zigzag fashion (manually or with a robotic arm) into the mold around the fingers. After stringing the fiber, a second sheet of the same material is placed over the fiber such that the strung fiber is sandwiched between the two sheets. Heat is then applied to seal the two sheets to form the composite fiber sensor pad.

In one embodiment, it is envisioned that the production design includes a continuous zigzag pre-grooved rubber/foam substrate which is encapsulated in a plastic casing after the installation of the fiber. The fiber is installed in the groove using UV-curable soft RTV or other equivalent adhesive. Selecting the right adhesive is useful to reduce microbending stresses in the fiber due to temperature variations that would otherwise contribute to excess optical signal attenuation. The groove depth in the foam substrate is approximately half the size of the overall diameter of the fiber (1 mm). In such a configuration, approximately half the fiber in the groove would appear above the substrate and the rest would become part of the substrate after installation. The rubber substrate, therefore, has two different sides. One side of the substrate has the fiber secured in the grooves (the sensing side), while the other side is flat without containing the fiber. In this fashion, the pad does not have raised rib-like structure but is relatively smooth providing further protection from damage. The sensor substrate is then be encased in an outer protective plastic sheet. The two outer sheets are heat sealed by conventional plastic welding technology, which advantageously prevents entry of liquids or moisture into the optical fiber sensor substrate while also achieving high strength. In operation, the fiber-exposed side of the substrate is placed directly under the patient to achieve good acousto-mechanical coupling.

In one embodiment of the pad, the optical fiber is used in a double-jacketed configuration, in which an extra protective coating is applied over the first jacket. This second jacket can provide additional mechanical strength to the fiber and prevents breakage since it limits fiber bending. The extra protective coating over the 900 micron polyester jacket increases the diameter of the fiber to about 1.8 mm. The increase in diameter of the fiber does not pose any problems in manufacturing. In fact, it is desirable to use larger diameter fiber because of the ease in handling the fiber during manufacturing process. Presently, the fiber is used without a second jacket and as a result requires custom repackaging and strain relief to protect the inter-connection between the pad and the electro-optic unit.

If the second jacket is applied on the fiber using pressure extruded from Optical Cable Corporation technology, the acoustic energy can still be efficiently coupled to the glass fiber with minimum coupling losses. This is achieved because the glass fiber is tightly coupled to all strengthening members (the buffer, first jacket and the second jacket), allowing efficient coupling of acoustic signals between any gaps or voids between the jackets and the buffer. Nevertheless, depending on the absorption coefficient of the jacketed material, one might expect some signal attenuation at the these low acoustic frequencies, which could be optimized by proper choice of material combinations.

Using a double jacket fiber configuration in the pad has two advantages. First, the process of custom interconnection between the pad and the electro-optic unit is eliminated. Secondly, the mechanical strength of the fiber is improved. Furthermore, in such an embodiment it may not be necessary to use a three-hole polyvinyl tubing to strengthen and protect the fibers at the transition interfaces and prevent breakage. This translates into cost savings because it reduces both the number of parts and the manufacturing steps, while increasing the reliability and quality of the sensor pad.

D. Fiber Optic Interferometers

The invention is designed to employ fiber optic interferometer can take many forms. More specifically, the Fabry-Perot, Mach Zehnder, Sagnac, or Michelson interferometers discussed below, can be configured in the invention to detect the aforementioned acoustical signals. Optically, the fiber optic interferometer determines the optical wave phase shift with respect to a reference optical wave phase. Optical phase shift(s) are generated via strain or pressure-induced length change and/or refractive index change in the fiber optic sensor arm, leg, or optical fiber path of the particular interferometer configuration. Herein, fiber optic interferometry can be described by the principle of two-beam interferometry, which allows the measurement of ultra-small differential phase shifts in the optical fibers as generated by the applied acoustic signals. The total phase delay ($\phi$) of light propagating through a fiber is given by:

$$\phi = nkL \qquad (1)$$

where n is the effective group refractive index of the fiber core, k is the en vacuum optical wavenumber ($2\pi/\lambda$) with $\lambda$ being the optical source wavelength, and L is the physical length of the fiber. The optical path length ($L_{OP}$) is given by:

$$L_{OP} = nL \qquad (2)$$

As with all single mode fibers above their natural cut-off wavelength, there are actually two orthogonal polarization modes that exist within the fiber mode field diameter; the space in and around the core where the electromagnetic wave fields are confined. Generally, due to birefringence effects that take place within bent or otherwise non-ideal deformed fibers, the polarization state is elliptical. Because of the high clad-to-core diameter ratio in single mode fibers, much of the orthogonal polarization mode power exists within the clad region of the fiber and, as such, can be easily tapped via evanescent field coupling devices, for example power splitters and combiners that are disclosed herein. However, in order for fringes to occur at maximum efficiency (visibility) all polarization states must be substantially identical at the point where the two beams are combined.

Ultra-small variations in the phase delay $\phi$ are found by the differentiation of equation #1 such that $$d\phi/\phi = dL/L + dn/n + dk/k \qquad (3)$$

of which the first two terms are related to physical changes in optical fiber caused by acousto-mechanical perturbations (heart, respiration, and/or physical movement) that are to be measured. Accordingly, the first two terms describe the transduction mechanism by which fibers act as sensors. Generally, changes in pressure, position (displacement), or temperature, for example, may result in different contributions to $\phi$ via the dL/L and dn/n terms.

Because the serial train of fringes is at maximum efficiency (visibility) only when the polarizations of the interfering beams are substantially identical, any polarization shift in one of the interfering beams with respect to the other will reduce efficiency. Such reduced efficiency, occurring over a period of time, leads to fading of the fringes; a problem that is addressed in detail elsewhere herein.

Fabry-Perot Interferometer

A common form of interferometer is the Fabry-Perot (FP) interferometer, which was first constructed in the late 1800s by Charles Fabry and Alfred Perot. It is a very useful device because it provides an extremely high resolution capability to measure displacements, and it can also be used as a spectroscopic device.

For purposes of illustrating the operating principles of a Fabry-Perot interferometer, a large-optic free-space Fabry-Perot multibeam interferometer will be discussed first. The large optic device comprises two parallel plane semi-reflecting mirrors which are separated by some distance, d. When a single coherent ray of light is launched from one side of the partially reflecting mirrored surface, it is reflected multiple times in the gap. For each reflection of the ray from the two interfaces, there is a transmitted ray produced. These transmitted rays combine to form a single fringe (vs. speckle) on the screen or the detector opposite to the launch side. The intensity of this fringe varies from bright to dark when the gap is varied, mechanically or the medium is altered, because the coherent light beam interferes either constructively or destructively as the separation of the gap (for example) is minutely (on the order of a fraction of light wavelength) varied, producing high or low intensity optical fringe. All monochromatic coherent rays launched at one angle combine to form a single fringe. If an optical detector is placed at this end, it will measure the variation of this single fringe intensity as a function varying gap separation.

For a Fabry-Perot interferometer to function properly when implemented in an optical fiber, the coherence length of the optical source must be much greater than the length of the sensing fiber. The reason is that light interference will occur at the receiving detector between the optical signals reflected from the first facet of the fiber and those transmitted through the second facet without reflection. Because of the round trip travel distance, the phase difference ($\phi$) between two successively transmitted waves at normal incidence is given by $$\phi \cong 4\pi n_f L/\lambda_0 \tag{4}$$

where L is the length of the sensing cavity (fiber), $\lambda_0$ is the operating wavelength and $n_f$ is the refractive index of the fiber. When the phase difference between two adjacent transmitted waves satisfies the interference condition 2L sin $\theta = n_f \lambda$; a standing mode is produced at the detector which is either dark or bright depending on the induced phase shift with respect to the reference phase shift (½ or an integer) with respect to the reference phase. In equilibrium, the standing mode does not change when there are no external forces present. However, when an external force is applied and/or the cavity length is altered, the standing mode is moved, because the transmitted waves realize an additional phase shift which changes further into the next cycle. Thus, when L is varied, the above equation is written as:

$$\Delta\phi \cong 4\pi n_f \Delta L/\lambda_0 \tag{5}$$

This variation in the phase difference produces a time varying fringe sweeping signal (dark-bright-dark-bright) at the detector. Thus the photo-detector measures displacement-velocity-acceleration signals generated by swept fringes which contains information about the rise/fall time of the applied acousto-mechanical signal and its repetition rate.

Figure 5:
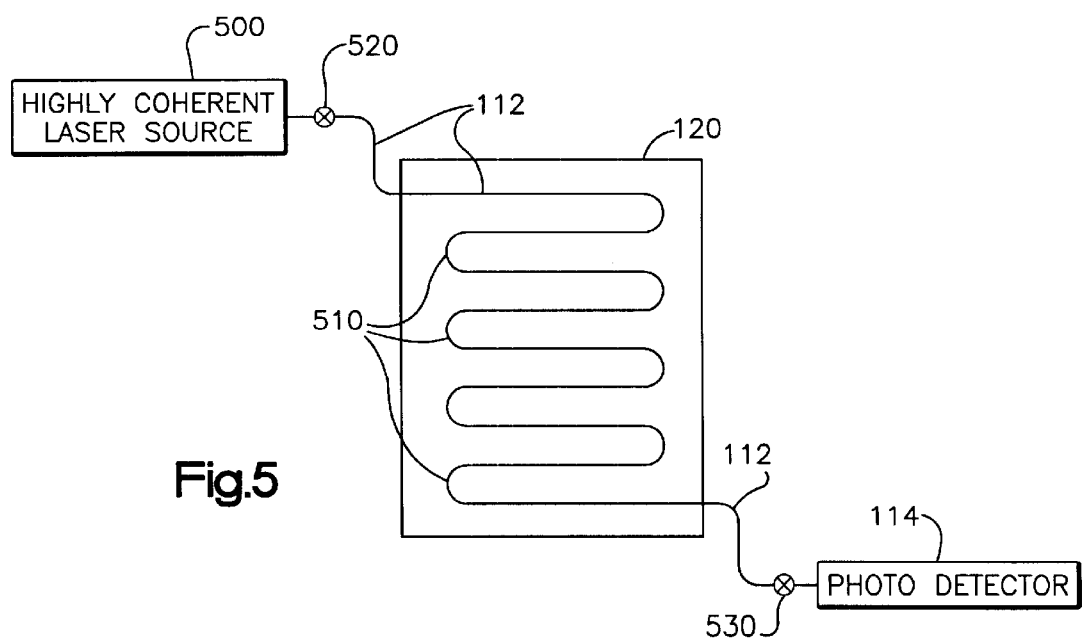
FIG. 5 is a diagram of the interferometer section of a fiber optic monitor implemented with a Fabry-Perot interferometer.

Reference is now made to FIG. 5, which is a diagram of a fiber-based monitor implemented with a transmissive Fabry-Perot fiber interferometer. A reflective Fabry-Perot can also be implemented via a coupler. A coherent laser source 500, such as a He—Ne laser or a DFB laser, supplies a laser beam that is coupled into the optical fiber 112. The optical fiber may be a single mode fiber or a multimode optical fiber made from fused silica, and for example, in one embodiment has a length of about 17 meters. An intermediate length 510 of the optical fiber (10 meters) is embedded into the sensor pad 120. The optical fiber has a first cleaved end 520 into which the laser beam from the laser is coupled, and a second cleaved end 530 is coupled to the photo-detector 114, which defines the cavity for the interferometer. In other words, the two cleaved ends of the optical fiber, which have a reflectivity of about 4%, serve as the two partially reflecting mirrors of the interferometer. Accordingly, the cavity medium is the amorphous glass of the optical fiber, which in one embodiment has a refractive index of about 1.457, and the physical length of the optical cavity is approximately 17 meters since the length of the fiber in this embodiment is about 17 meters. In operation, the incident light from the laser source coupled into the optical source propagates into the core and is partially reflected from the far distal end (the second cleaved end) of the fiber. However, a part of this beam is also transmitted through the second cleaved end and out of the fiber. The reflected light returns to the first cleaved end and then is reflected again. In this fashion, the transmitted light comprises two or more propagating longitudinal cavity modes, which mix and interfere at the photo-detector. The transmitted modes interfere constructively and destructively over time as the length of the fiber is minutely changed by cyclic acousto-mechanical pressure impulses, for example, generated by the heart, respiration or physical movement and applied to the fiber in the transverse direction.

The intermediate part of the fiber (about 10 meters) is configured within the sensor pad in a zigzag fashion extending from the top of the sensor to the bottom. The pad is placed under the patient (FIGS. 3 and 4) in order to detect the acousto-mechanical signals generated from heart, respiration and any physical movement. In any particular embodiment, the configuration of the optical fiber within the sensor pad is designed to provide effective coupling of the acousto-mechanical signals into the optical fiber. The detection and isolation of these three signals and post-analysis provides the means to sense apneic events or other abnormalities in patients.

Mach Zehnder Interferometer

Figure 6:
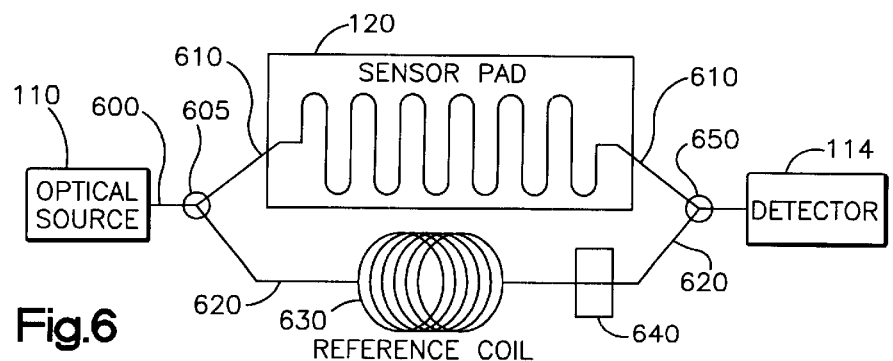
FIG. 6 is a diagram of the interferometer section of a fiber optic monitor implemented with a Mach-Zehnder interferometer.

Reference is now made to FIG. 6 which is a diagram of a Mach-Zehnder interferometer. The optical source 110 supplies coherent or incoherent light 600 which is divided at a first fiber coupler 605 between a first fiber arm 610 and a second fiber arm 620. The first fiber arm 610 extends through the sensor pad 120 and second fiber arm includes a reference coil 630 and a polarization controller 640. The polarization controller can be placed in the sensor arm as well. The purpose of the polarization controller is to maximize signals through all possibilities of polarization in order to prevent polarization induced signal fade. The first and second fiber arms are combined at a second optical coupler 650, and the combined output is then supplied to the detector 114. For the Mach-Zehnder interferometer to operate efficiently, the first and second fiber arms must have nearly the same length, and the coherence length of the optical source must be approximately equal to the actual length difference between the two fiber arms. If the coherence length is too short the fringe pattern will be weak or non-existent, and if the coherence length is too long, phase noise will dominate the intensity variations.

The acousto-mechanically-enhanced pressure variations on the sensor pad 120 create corresponding minute changes in the intermediate length of the fiber in the sensor pad, compared with the reference fiber. When this difference is compared to the optical wavelength of the optical source, tens, hundreds or even thousands of wavelengths may be affected by the pressure changes. By combining the two optical signals at the second coupler and counting the fringe patterns, a conversion from pressure to fringe counts can occur. These fringe patterns may start as very slow changes as is the case with breathing, a little faster for heart rate and very fast for physical movement.

The output intensity of the interferometer incident of the photo-detector may be expressed as:

$$I = <E_r^2> + <E_s^2> + 2<E_r E_s> \tag{6}$$

where < > denotes the time average over a period much longer than $2\pi/\omega_o$ and $E_r$ and $E_s$ are the optical fields at the photo-detector(s). The intensity varies as the phase of the two signal varies. The efficiency or fringe visibility of the interferometer (assuming identical polarization states exist at the output coupler) is given as:

$$V = (I_{max} - I_{min})/(I_{max} + I_{min}) \tag{7}$$

The actual value of V depends ultimately on the self-coherence function g(t), which is given by $g(t) = \exp[-|t|/t_c]$, where t is the differential optical propagation time delay between the reference and signal paths and $t_c$ is the source coherence time. Therefore, V is always reduced by the factor g(t). For this reason, the differential propagation time delay between the fiber paths is adjusted to be much less than the coherence time (t<$t_c$). Therefore the factor g(t) approaches unity and V is maximum, as determined by the polarization states of the two beams at the combining power coupler.

For fiber-based ASE (Amplified Stimulated Emission) sources, semi-conductor laser diodes without Bragg diffraction gratings, ELEDs or LEDs, the coherence length is fairly small, on the order of hundreds of microns to a few millimeters, and therefore the length difference between the two fibers that provide the two optical paths of the Mach Zehnder Interferometer must be on this order. For some light source choices, the fiber length differences must be measured extremely accurately in order to provide a highly sensitive monitor. One way of accurately measuring this length is to utilize high resolution optical time domain reflectometers that can provide sub millimeter resolution. Another way of measuring the length, is to use conventional measuring rulers or gauges, which are not as accurate, and would limit the use to a laser diode having longer coherence length than an ELED or LED.

Sagnac Loop Interferometer

Figure 7:
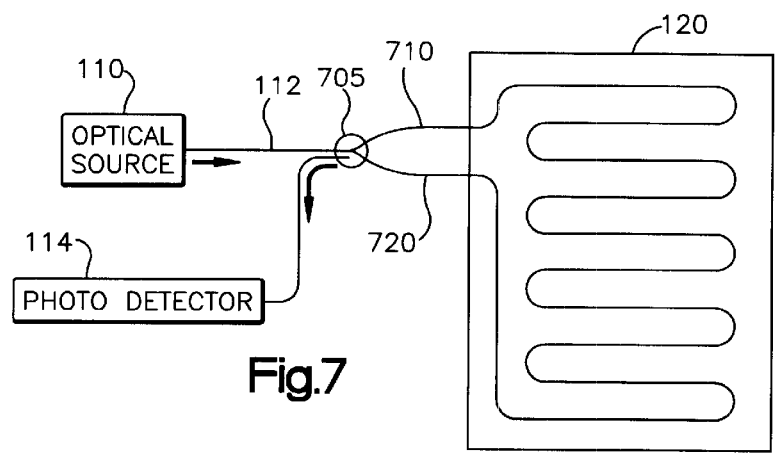
FIG. 7 is a diagram of the interferometer section of a fiber optic monitor implemented with a Sagnac interferometer.

Reference is now made to FIG. 7, which is a conceptual diagram of a fiber optic monitor implemented with a Sagnac interferometer. Because of its common path architecture, a Sagnac interferometer does not convert source phase noise into intensity noise, thereby eliminating a major source of the low frequency noise present in Mach-Zehnder sensors. Also, because of the common-path, and to further reduce noise, Sagnac interferometers can use inexpensive, broadband high-power sources, such as ELEDs, LEDs, ASEs, fiber superfluorescent, and superluminescent diodes, in place of generally more expensive narrow linewidth lasers. In the Sagnac interferometer, light from the optical source 110 is coupled into both ends of the optical fiber at a coupler 705. Particularly, the light is coupled from the coupler 705 in phase into a first end 710 and a second end 720. Light signals coupled into the first end propagates through the optical fiber to the second end, and light signals coupled into the second end propagate in the opposite direction through the optical fiber to the first end. Both of the light signals then exit at the coupler 705 and propagate together through a fiber section 730 to the photo-detector 114, where the time-varying fringes are produced and measured. In the Sagnac interferometer, the phase shift is measured between the light going clockwise (CW) to the light going counterclockwise (CCW) in a loop of fiber where optical signals are launched in opposite directions in phase.

Figure 8:
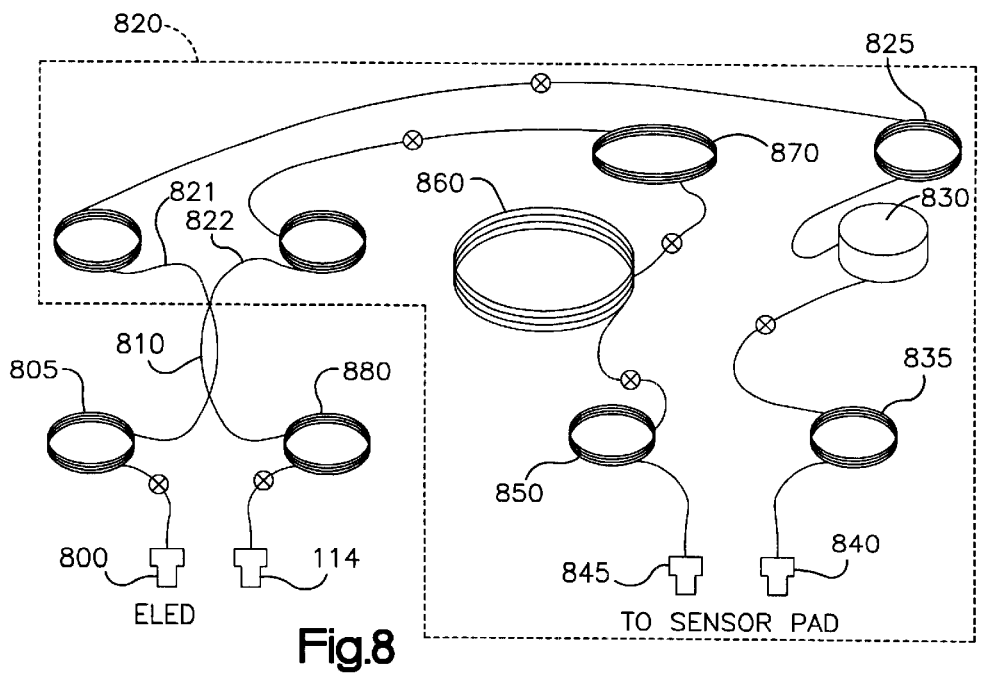
FIG. 8 is a diagram of an alternative embodiment of the interferometer section of a fiber optic monitor implemented with a Sagnac interferometer.

Reference is now made to FIG. 8, which is a diagram of one embodiment of a Sagnac interferometer. The light source comprises an ELED 800 that is coupled to inject light into a first length 805 of optical fiber. A 50/50 coupler 810 is connected to the first length 805, and divides the light so that it is injected approximately equally between a first end 821 and a second end 822 of a fiber optic loop defined within the box 820. Beginning at the first end 821, the loop includes an optical fiber length 825 that has a suitable phase modulator 830 attached thereto. After the phase modulator 830, another length 835 of optical fiber is connected at a first pad interconnect 840 to one end of the optical fiber in the sensor pad 120 (see FIGS. 5, 6 for example). The other end of the optical fiber in the sensor pad is connected to a second pad interconnect 845, which is coupled to another length 850 of optical fiber. This optical fiber 850 is connected to a delay coil 860 that has a length that defines a large percentage of the overall length of the entire loop length inside box 820. The delay coil 860 is coupled to a depolarizer 870, which in turn is connected to the second end 822 of coupler 810.

The counter-clockwise (CCW) propagating beam, after traveling through the delay loop 820, is combined at the 50/50 coupler 810, and then propagates along a final length 880 of optical fiber to the photo-detector 114. The clockwise (CW) propagating beam travels first through the delay loop, fiber, and then through the, sensor fiber, whereas the CCW beam travels through the sensor fiber first and then through the delay loop fiber. During the time delay period between the arrival of the CW and CCW beams at the detector, the perturbing the perturbation induced phase modulation in the sensor fiber changes. This change in phase modulation is directly proportional to the phase difference between the counter-propagating beams, which generates a serial train of optical fringes when the beams combine and interfere at the power coupler.

In an alternative embodiment, the Sagnac interferometer can be implemented to operate in a reflective mode where the transmissive loop is replaced by a single fiber with a mirror at the distal end. Similarly, a single coupler/splitter approach may also be employed to operate in a transmissive mode. Many other configurations are known, some of which are described herein.

Theoretically, if a physical perturbatory signal of angular frequency ω induces a phase modulation $f_s \cos(\omega t)$ in the sensor fiber loop, the resulting phase modulation between the interfering beams at the sensor $f_{in}$ (t) is then given by:

$$f_{in}(t) = f_s \cos(\omega t) - f_s \cos[\omega(t + T_{delay})] \quad (8)$$

$$= 2f_s \sin[\omega T_{delay}/2] \sin[\omega t + \omega T_{delay}/2] \quad (9)$$

where $T_{delay}$ is the time delay between the arrival of the CW and CCW beams at the sensor itself. Thus, the amplitude of $f_{in}(t)$ is a function of the sensor phase modulation $f_s$ and the product of the perturbatory angular modulation frequency with the loop time delay. This differs from the Mach-Zehnder sensor in which the amplitude of $f_{in}$ (t) is a function of only the sensor phase modulation $f_s$.

Maximum sensitivity can be achieved in the Sagnac interferometer sensor when the product ω $T_{delay}$ is an odd multiple of π. The perturbation frequency that makes this product exactly π, which is the lowest frequency at which maximum sensitivity is achieved, may be called the "ideal" frequency of the loop. For the ideal loop frequency to be below about 7 kHz, which is the frequency regime of interest for most human and animal body motion sensing applications, a time delay of at least 50 microseconds, and therefore a delay loop length of about 7 km is required. In one embodiment, by trading off the frequency response and delay loop length, the Sagnac sensor was designed with approximately a 500 meter delay loop and about 20 meter sensor loop.

The phase modulator 830 is utilized to translate the acousto-mechanically-modulated light signal out of the DC region into an AC signal. The phase modulator may be employed in one or both arms of the interferometer. Such phase modulators are commonly used for low frequency audio signal systems. Phase modulators can have many forms, such as a fiber stretcher, which is typically constructed by winding an optical fiber around a cylindrical piezoelectric transducer. The piezoelectric material utilized is typically of the lead-zirconate-titanate (PZT) family of piezoelectric crystals. Other forms of such bulk crystal modulators may be employed, such as PZT disk stacks and bars, which allow for non-coiled fiber stretching. In these PZT embodiments, the fiber to be stretched is linearly attached to the surface of the crystal along the primary polling orientation of the crystal for maximum mechanical force as a function of applied voltage across the crystal electrodes. The PZT cylinders, however, act on the helical turns of fiber via hoop or radial modes of crystal polling. Such phase modulator/shifters serve the function of a voltage-controllable-phase shifter.

The type of optical source plays a role in achieving the ultimate noise performance of any fiber interferometer. As mentioned earlier, the coherence length of the source must be much longer than the length mismatch between the two optical paths of the interferometer. In fact, any mismatch in length between the sensing and reference paths, whether delayed or not, leads to increased intensity noise through a coherent interference process where the phase noise is converted to intensity noise. The phase noise of the source is ultimately the limiting noise factor if any path mismatch is present in the interferometer.

For these reasons relatively broadband sources (tens of nanometer FWHM), such as LEDs, ELEDs, superluminescent diodes (SLD), and amplified spontaneous emission (ASE) superfluorescent, are typically employed in perfectly matched path interferometer circuits, such as the Sagnac loop. Contrarily, narrower band sources (~0.1–5 nm), such as Fabry-Perot lasers, DFB and fiber lasers, are typically employed in slightly mismatched circuits, as are realized in Michelson and Mach-Zehnder configurations.

Signal Fading

There are at least two ways in which signal loss can occur in optical fiber interferometers, not including insertion losses from various fiber components in the optical interferometer circuits. These are: 1) slowly time varying differential phase shifts due to, for example, ambient temperature and pressure fluctuations; and 2) differential variations in the polarization state within the fiber paths, which also can be due to ambient changes in temperature and pressure, but are largely due to uncontrolled rotation/twisting and bending in the fiber.

Twisting and bending in an ordinary single mode, non-polarization maintaining fiber, can lead to birefringence effects in the fiber between the two degenerate orthogonal polarization modes. The resulting differential phase velocities of these two modes produce polarization rotation in one path with respect to the other path, which leads to an effective dot product of near zero between the two interfering optical fields within the output coupler or at the detector, thus producing little or no detectable interference fringes, from an otherwise a state of good interference. This reduction in detectable interference fringe signals, due to polarization effects, is generally called "polarization fading or signal fading".

In fiber optic interferometers, the signal fading can be minimized in many different ways. For example, by replacing the entire length of the single mode fiber with a polarization-maintaining (PM) fiber can eliminate this problem. However, the cost of using the PM fiber throughout an interferometer is prohibitive for most low cost embodiments. Alternatively, either passive depolarizers or actively controlled polarization controllers may provide a more cost effective solution to adjust the polarization states of the signal and reference paths to minimize signal fading.

The depolarizers or polarization controllers can take a variety of forms, some of which are discussed elsewhere herein. For example, the passive depolarizer may consist of two sections of polarization maintaining (PM) fibers crossed at 45 degrees; whereas controllers may include devices such as 1) multi-axis fiber squeezers to produce controlled birefringence; 2) resistive heater using bimetallic elements to produce controlled birefringence; or 3) high speed polarization mixers or scramblers. These controllers or depolarizers when used in fiber interferometers can provide compensation to cover the complete Poincare Polarization Sphere of the numerous polarization state possibilities.

In operation, the optical fiber in the sensor pad 120 may be subjected to phenomena such as temperature changes and pressure differentials that tend to shift the polarization of the optical signal propagating throughout. As discussed briefly above, any polarization shift in one of the interfering beams with respect to the other will reduce interference efficiency and cause fading of fringes over time because the interference is at maximum efficiency (visibility) only when the polarizations of the interfering beams are substantially identical. Such polarization-induced fading problems can substantially degrade the signal-to-noise ratio and thereby degrade the effectiveness of the monitor. Accordingly, many embodiments of the fiber optic monitor include features to reduce fading, such as the depolarizer 870 shown in FIG. 8. This depolarizer 870 is generally passive or if a polarization controller is used, it may be dynamically driven at frequencies at least twice of any present in the sensor or phase modulation circuits.

In the Mach-Zehnder interferometer embodiment shown in FIG. 6, it is known that the two optical path lengths in an interferometer must be very closely matched. Even if lengths are matched at room temperature during the manufacturing process, temperature gradients between the sensor pad and the reference coil along and/or changes in pressure on the sensor pad independently can shift the polarization of the light beam in one of the fibers with respect to the other. This can be enough to cause the light intensity to fade as a result of the polarization state vector of one arm moving from a parallel orientation to a perpendicular orientation of respective vertical and horizontal components, resulting in cancellation of the desired signal. To minimize this fading, it is necessary to adjust the polarization state of the two arms of the interferometers such that the dot product of the interfering beams in the output coupler is as close to unity as possible. Again, this may be accomplished by employing the polarization controller 640 (FIG. 6), which is generally placed in one arm of the interferometer. To maximize the signal, the polarization controller 640 is adjusted and set once if no further changes are required in fiber circuit physical geometry. However, if the physical layout of one or both paths of the interferometer must change, for example due to deployment logistics or external perturbations, then the polarization controller set-point must change accordingly. For this reason in this embodiment, an active slow speed servo-loop feedback circuit is implemented along with the polarization controller in order to maintain maximum fringe visibility.

In the Sagnac interferometer embodiment, which generally utilizes a broadband source, two short sections (less than a couple of meters) of crossed polarization maintaining fibers provide a passive (without quasi-static servo), low cost solution suitable for maintaining the polarization states via depolarization as a function of $\delta\lambda$. On the other hand to achieve equivalent performance in interferometers using narrow band sources, the length of each section of the PM fiber must be substantially increased. For these interferometers, the fiber squeezer type polarization controllers with active control may be more effective in maintaining the proper polarization states and reduce signal fading.

Electro-optic Unit Embodiment

Figure 9A:
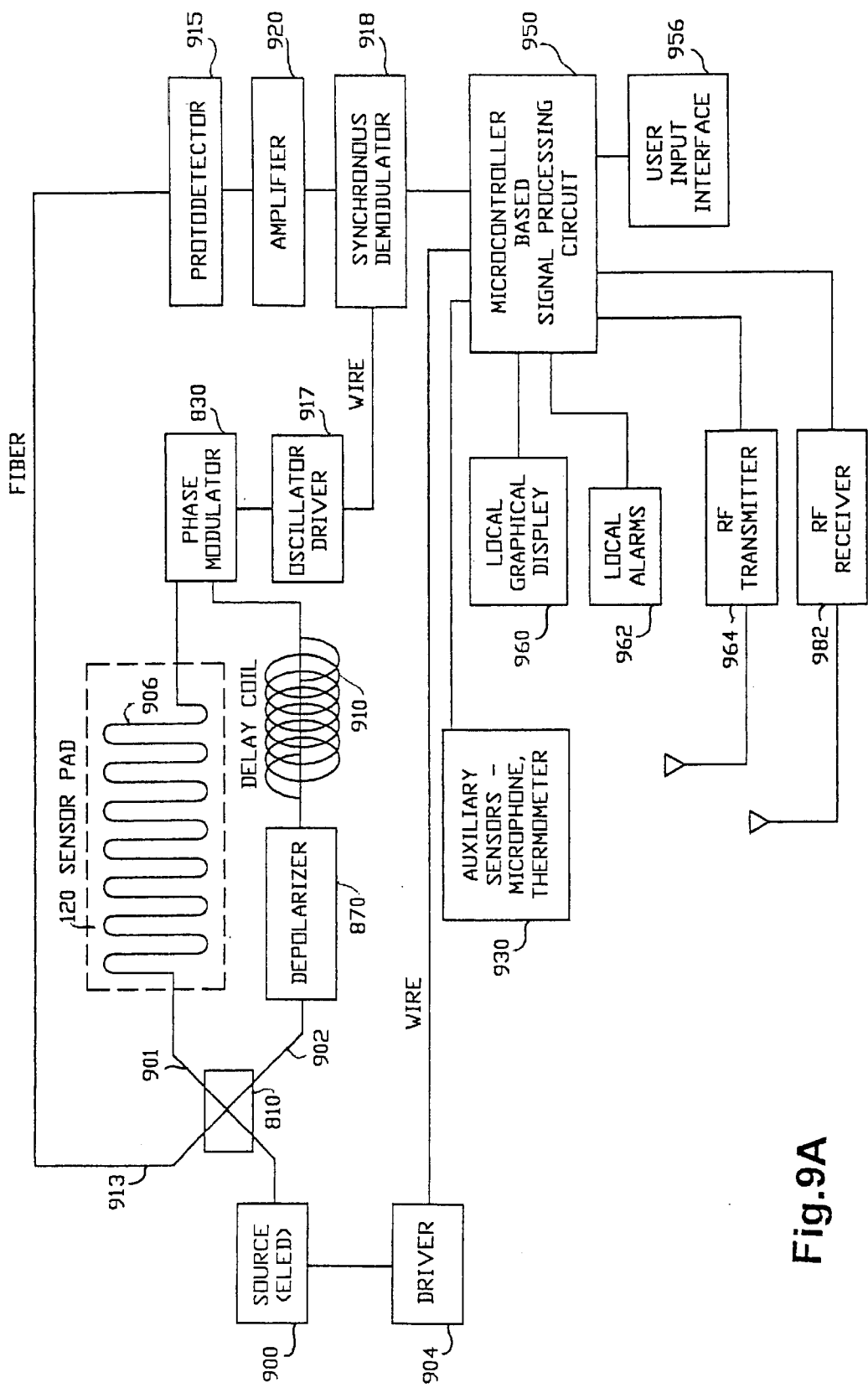
FIG. 9A is a block diagram of the interferometer and associated processing circuitry for one embodiment of a fiber optic interferometer-based sensor in a Sagnac Loop configuration suitable for detecting heartbeat, respiration, and physical movement.
Figure 9B:
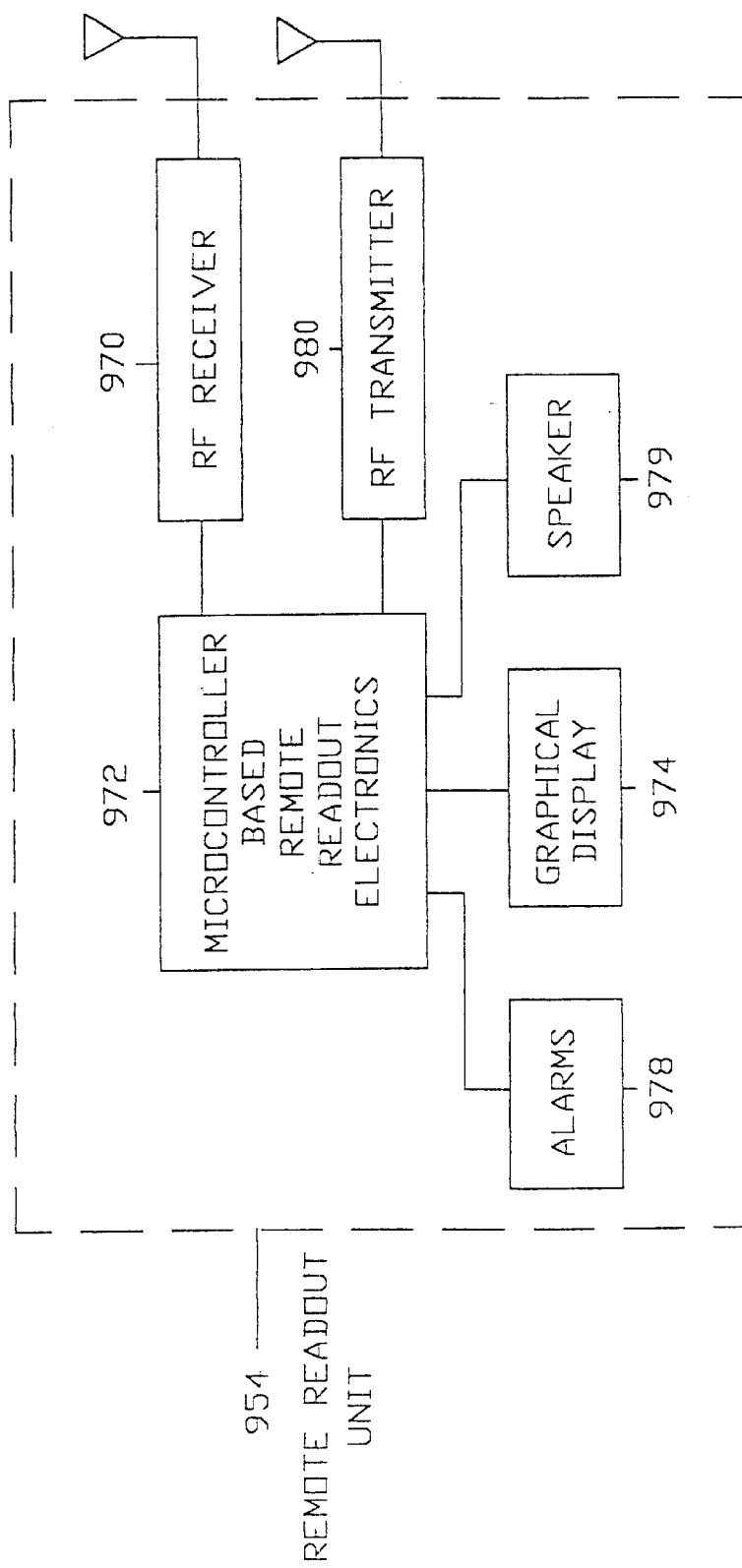
FIG. 9B is a block diagram of a remote receiver unit for receiving separated signals from the processing circuitry of FIG. 9A.

Reference is now made to FIGS. 9A and 9B, which form a block diagram of one example of a fiber optic interferometer-based monitor in a Sagnac Loop configuration suitable for detecting and displaying heart, respiration, and physical movement signals locally at the sensor via the electro-optic unit and remotely via a remote readout unit.

A broadband optical source 900 such as an ELED supplies optical radiation to a continuous Sagnac loop including a first end 901 and a second end 902 of optical fiber. The optical radiation is injected into the two ends via the optical coupler 810. A suitable source driver 904 drives the optical source 900 which is controlled by a micro-controller 950. The first end 901 is connected to an optical fiber section 906 arranged in an approximate zigzag configuration within the sensor pad 120. At its other end, the optical fiber 906 is connected to the phase modulator 830, described with reference to FIG. 8. The phase modulator 830 is connected to a fiber delay coil 910, which is then connected to the depolarizer 870, described with reference to FIG. 8. The phase modulator 830 is driven by an oscillator 917 at a suitable frequency (approximately 30 kHz in one embodiment), and is used to add a high AC carrier frequency to the optical signal. The depolarizer 870 is connected to the second end 902 of the optical fiber. The depolarizer 870 is used to reduce optical signal fading resulting from polarization changes. The CW and CCW beams exit the Sagnac loop from the coupler 810, and are supplied via an optical fiber 913 to a photo detector 915 which is arranged to detect the serial train of fringes from the output of the coupler 810. The photo-detector 915 converts the optical signal to an electrical signal, which is applied to the amplifier 920, that in one embodiment includes a conventional DC-coupled trans-impedance amplifier as the first stage. The interferometer generally produces a DC offset signal along with an AC signal if the splitter/coupler ratio is not precisely 50/50. To remove the DC offset signal, the output of the first stage of the amplifier 920 is AC-coupled to a second stage of the amplifier. The amplified signal is then passed on to a synchronous demodulator circuit 918 that uses a reference signal from the oscillator driver 917 to strip away the AC carrier frequency from the desired signal. The recovered signal is passed from synchronous demodulator 918 to the microprocessor based signal processing circuit 950.

In the speckle pattern prior art, to optimize detection sensitivity the output fiber 913 and the photo detector 915 are often arranged to receive only a fraction of the light from the fiber 913 containing the speckle pattern. In such a prior art case, the raw electrical signal from the photo-detector would represent the average intensity of the sample portion of the speckle pattern. In contrast, in one embodiment of the present invention, the output fiber 913 and the photo-detector 915 are arranged so that the photodetector collects the entire cone of light (i.e. all the energy) emitting from the fiber 913 rather than just a portion. If the entire cone of light is not collected, it would degrade the performance as a result of reduced signal to noise ratio. By collecting the entire light cone and tracking the phase of the modulated frequency via the synchronous demodulator, it is possible to achieve a very high signal to noise ratio. The output fringe signal from the interferometer can be tracked with the micro-controller counter.

Signal processing techniques, which can be accomplished by various approaches known to those skilled in the art, are employed to separate the signals from the synchronous demodulator 918 into heart rate, respiration and movement components. In one such signal processing technique, each component is analyzed to determine whether or not it falls within acceptable boundaries. The acceptable boundaries are thresholds that can be pre-programmed into the processor depending on the specifics of the patient being monitored. The results of the analyses of each component are output in a suitable manner, such as by display on a local graphical monitor 960. The display can range from a simple numeric readout of the present rate or be as involved as an LCD, LED bar graphs or oscilloscope-type displays of the signal level vs. time, for example. A user input interface 956 is used to program the microprocessor for the type of local display desired. If any of the monitored parameters go outside of the preset threshold boundaries, the micro-controller activates one or more local alarms 962.

The system shown in FIG. 9A provides remote signal outputs also. The microprocessor-based signal processing circuit 950 interfaces to an RF transmitter 964 and receiver 982 that provide communication with a remotely located readout unit 954, shown in FIG. 9B that includes a micro-controller 972 connected to a RF receiver 970 and an RF transmitter 980. In addition to the interferometer signal, the signal processor 950 may also monitor and report on the inputs of various auxiliary sensors 930 such a microphone, thermometer, etc. to the remote unit. In response thereto, the micro-controller 972 located in the remote unit 954 generates signals supplied to an LCD display 974, an alarm function 978 such as a buzzer or vibrator. The signals from a micro-controller may also be supplied to a voice chip that announces the alarm condition via a speaker 979. Alternatively, chart recorders or computerized data collection and display systems may be used to record any of the signals both locally or remotely via modems or via other communication systems.

The communication link between the sensor pad 120 and the auxiliary sensors 930 (via the signal processor 950) to the remote unit 954 that is shown as RF in FIG. 9A can alternatively utilize infrared, AC power line carrier current, phone line, direct wire, optical, and etc. Also, many types of modulation could be used, such as AM, FM, FSK Spread Spectrum, Time Division Multiple Access (TDMA), Code Division Multiple Access (CDMA) and others. In order to provide bi-directional communication and implement a system for fail-safe handshaking to guarantee the integrity of the communications link, the RF transmitter 980, connected to the micro controller 972 of the remote unit 954, transmits to a second receiver 982 that is connected to the micro controller 950 of the electro-optic unit. For example, the microcontroller in the signal processor 950 can periodically send a message to the remote micro controller 972 and receive a handshake message via the return link from the remote transmitter 980 and the base unit receiver 982. In one embodiment, if the remote controller does not receive a communication in a pre-determined time, it can set off an alarm to notify the user that communication has stopped.

Under some circumstances for battery operated systems, the battery life may be extended by pulsing the optical source at frequencies much higher than the phase modulator frequency. For example, if the phase modulator frequency is 30 kHz, the source may be modulated at 500 kHz with a 5–10% duty cycle. Care should be used in selecting the optical source modulation frequency to minimize signal degradation. Modulating the optical source may also be helpful to increase the signal over noise ratio, especially when the optical path losses are large and the detection sensitivity low resulting in marginal signal over noise ratio. For example, a marginal signal over noise ratio may occur when the optical source cannot be driven any harder in CW mode to overcome the optical path losses and detector sensitivity for a required bit error rate (BER). In such a case, the optical source power may be pulsed in order to increase power in proportion to a reduction in duty cycle. The microcontroller-based signal processing circuit 950 may be used to drive the optical source 900 with a narrow pulse width via the driver 904.

The remote unit 954 can comprise many different embodiments and configurations. In one embodiment, the visual and audio signals are displayed on the remote unit. An alarm is triggered upon any of the following events: the infant is not in the crib, system or fiber failure, absence of physical movement, absence of respiration or absence of heart beat, abnormal respiration, abnormal heart beat or any combination thereof. The alarm system may be designed so that it is not triggered by electrical noise or presence of acousto-mechanical noise. For example, this system could be implemented as an infant monitor that indicates his/her well being by providing heart beat, respiration and body movement or a combination thereof even when the infant is sleeping. Additionally the microphone sensor when integrated into the e-o unit or in the pad can detect and transmit normal sounds of the infant, especially when the infant is awake and moving around in the crib. The remotely located unit integrated with the speaker and the alarm provides the display with actual numbers and flashing indicators of the respiration, cardiac activity, body movement, cry/voice signals and monitor status. The bi-directional fail-safe communication system is used to maintain contact between the sensor system and a remote unit carried by the guardian, parent or care giver.

In another embodiment, the optical source 900, photodetector 915, and the associated circuitry such as preamplifier, filters and signal processing electronics shown in FIG. 9A may be situated in a single electro-optic unit. The sensor pad 120 and the electro-optic unit may be remotely located from each other by means of an inter-connect fiber cable. The light from the source located in the electro-optic unit is transported to and from the pad via a two fiber inter-connect duplex cable. The entire system excluding the sensor pad 120 can then be situated in one remote location with the caregiver, thereby precluding the need for a communication link.

Signal Processing and Separation of Signals

Many forms of signal processing can be utilized for the separation and conversion of the analog signals into digital signals that subsequently can be analyzed and displayed in various ways. A low cost approach suitable for in-home application is to use multi-pole filters, including a low pass filter and a high pass filter in the signal processing circuit 950 for the separation of movement from heart rate and breathing, and then using an A/D converter at the analog input of a single chip micro-controller to perform the analog to digital conversion. Once digitized, the rate can be calculated by the microcontroller in the circuit 950. The low pass filter separates the heart rate and breathing signal from the physical movement signal because these are lower in frequency compared to the movement signal. Therefore they can be easily processed by a low cost one-chip micro-controller where preset thresholds provide this functionality. Because in home environment, the movement signal is used to detect infant activity, it does not require highly accurate processing. The high pass filter is adequate to allow separation of the movement signal from the other two signals. On this channel, thresholds limits can be monitored using an analog integrator and comparator.

Figure 10:
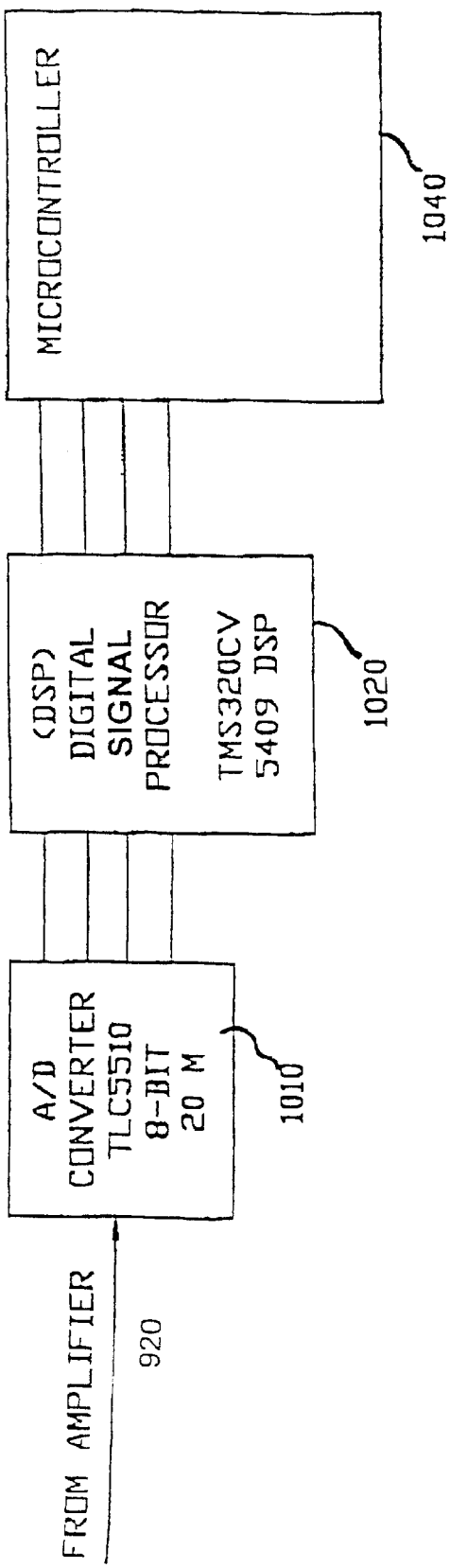
FIG. 10 is an alternative embodiment of a signal processor including digital processing circuitry suitable for uses such as where individual signals must be separated in the presence of physical movement.

Reference is now made to FIG. 10 which is a block diagram of an alternative embodiment of the microcontroller-based signal processing circuit 950 that includes digital processing circuitry suitable for applications where reliable signal separation of the individual signals is required. For example, in hospital environment it is necessary to separate the heart beat signal from the respiration signal in the presence of the physical movement to better predict the onset of apenic event. The digital signal processing circuitry, such as shown in FIG. 10 can eliminate the need for the multi-pole filters and can provide high performance separation of the individual signals. In the embodiment shown in FIG. 10, the output from the amplifier 920 is supplied to the DSP processing circuit that comprises the AID converter 1010, such as an 8 -bit or 16 -bit, 20 million sample per second A/D converter available from Texas Instruments (TLC5510). The digitized output is then supplied to the DSP circuit 1020 such as a DSP available from Texas Instruments (TMS320CV5409) although many other DSPs could also be used. The DSP 1020 provides a parallel input to a microcontroller 1040. The DSP includes routines that perform the multi-pole filtering and threshold functions. The microcontroller 1040 can then do the counting for the display of the rate information.

The DSP 1020 may include algorithms to account for a variety of effects and signal processing problems. For example, the algorithms may be designed to reliably detect and isolate the heart beat and respiration signals in presence of patient's physical movement when such noise is present over an approximate period of about three seconds (which is a low end for infant apnea alarm delay setting). Physical movement induced noise is generated when an arm or a leg or body of a patient rubs the pad. Because the physical movement noise signal amplitude is generally much greater than the respiration or the cardiac activity signals, it may result in data "washout" over the signal tracking period. If the noise tracking period is selected to be about three seconds, it will introduce a data latency of about three seconds in the heart and respiration signals. This may be reasonable provided the algorithms can track signals from the next cycle while displaying signals from the previous cycle. Pattern recognition techniques would allow separation of the heart signal from the respiration. However, if the physical movement noise period exceeds three seconds, the signal tracking period may be increased. The maximum tracking period may be limited to less than seventeen seconds based on upper end of apnea alarm delay setting of twenty seconds. Under such conditions, the data latency will be seventeen seconds which must return to three seconds once the apnea event has passed. Alternatively, other advanced signal processing techniques such as auto time correlation, fast Fourier transforms, artificial intelligence, neural networks, fuzzy logic, and others may be implemented to separate the heart from respiration signals in presence of the physical movement noise signal.

Additional features of the algorithms may be to separate an infant's low heart rate from increased respiration rate. Under some conditions these two rates may be identical, resulting in false alarms. Separation may be accomplished by sampling higher frequency components associated with the heart beat which are generally absent in respiration signal. For example, the low heart rate (bradycardia) in infants ranges from 40 beats per minute (bpm) to 130 bpm which can overlap with the typical respiration rate ranges from 1 breath per minute (bpm) to 99 bpm. Similarly, in adults the low heart rate is 30 to 100 bpm which somewhat can overlap with 15 to 30 breaths per minute.

The system algorithms may be designed to include variable alarm setting capability. For example, because the high heart rate (tachycardia), in infants ranges from 150 to 300 bpm whereas in adults it is 100 to 250 bpm, the heart alarm delay in each case may be adjusted from about three beats to seven beats. In a similar way, the apnea event alarm delay setting may be made variable and set to 3 to 40 seconds for infants (20 seconds is typical) and 10 to 25 seconds for adults.

Similarly, the algorithms may be designed to identify shallow respiration rates from no respiration that causes reduction of heart rate (bradycardia). Many other conditions may be programmed providing reliable monitoring while achieving reduced false alarm rates compared to previous systems.

Sample Test Data

FIG. 11 is a graph of experimental data over a period of about twenty seconds of a normal infant, obtained using one interferometric monitor as described herein, in an implementation in which the heartbeat and respiration are output in the form of a combined signal 1100. The horizontal axis shows time, and vertical axis shows amplitude of the combined signal. In the graph of FIG. 11, it can be seen that the weaker but higher frequency heartbeat signal is superimposed upon the stronger, lower-frequency respiration signal. Particularly, the lower-frequency respiration signal in FIG. 11 has a period shown at 1110 of approximately five seconds, while the higher-frequency heart beat has a period shown at 1120 of less than about one second, which is normal for this patient.

FIG. 12 is a graph of experimental data over a period of about twenty seconds of the same infant, obtained using the same interferometer monitor as described herein but with a different sensor pad configuration than in FIG. 11, in an implementation in which the heart and respiration signals are output in the form of a combined signal 1200 in which the heart signal is better defined than the respiration signal. As in FIG. 11, the horizontal axis shows time, and vertical axis shows amplitude of the combined signal. In the graph of FIG. 12, it can be seen that the higher frequency heart signal has a much larger amplitude than in FIG. 11, which results from adjusting certain parameters in the pad and optical fiber to strengthen the coupling of the higher-frequency acousto-mechanical signals into the optical fiber. The higher-frequency heart signal has a period shown at 1120 of less than about one second, which is normal for this patient, while the lower-frequency respiration signal has a period of approximately 5 seconds, which is detectable but difficult to measure precisely compared to FIG. 11 sensor configuration.

Alternative Embodiments

It will be appreciated by those skilled in the art, in view of these teachings, that alternative embodiments may be implemented without deviating from the spirit or scope of the invention.

For example, a display system could be used at either the sensor end (at the electro optic unit) or the remote receiver, or both. Monitoring and display of the signals generated by the fiber optic-based sensor might include a computer-like display such as a Liquid Crystal Display (LCD). Such a display system may comprise a graphical display, for example, the actual numbers representing heart rate, breathing rate and number of moves in a given amount of time. Heart signals can be displayed in digital form (actual numbers) such as beats per second or in graphical form such as an oscilloscope trace showing the classical wave shapes. Breathing rate can be displayed in actual numbers such as breaths per minute or in graphical form such as an oscilloscope trace showing the classical wave shapes. Apnea or transient suspension of respiration is detected in the microprocessor and which triggers an alarm. Voice chips (integrated circuits) could be programmed with the users own voice to the alerted situation. For example, a voice chip can be utilized to record an alarm message in the guardian, parent or caregivers own voice. When the alarm condition is transmitted to the remote monitor the voice message would then be played back.

Warning lights or LED's could flash at the heart rate, breathing rate or movement. The alarm function may take many forms as used presently in remote pagers. These may contain one or more of the following types of alarms: 1. Buzzer or Beeper, 2. Vibrator, 3. Flashing Lights or LED's, 4. LCD Display showing a visual message or graphical display, 5. Voice Encoded Messages.

In an alternative embodiment, two or more fiber sensors may be used within a single pad for isolating different acousto-mechanical sources and/or to improve accuracy. For example, in the detection of obstructive apnea, the property that the abdominal vs. chest/crib compartmental excursions are different can be utilized. Because impedance sensors rely on resistance measurements of skin, they can not be localized sufficiently to eliminate cross coupling. As a result, noise is generated in the detection system which imposes difficulty in isolating the two signals from the chest and abdomen. By utilizing two fiber optic sensors in the two local areas within the pad in such a way that one detects abdominal breathing while the other detects chest breathing, it may be possible to detect the onset of obstructive apnea.

The fiber optic monitor can be used in conjunction with other sensors such as a camera, an EKG, an oxygen sensor, and/or a carbon dioxide sensor, temperature sensor. For example, a conventional monitor such as a finger-situated monitor that senses saturated oxygen, carbon dioxide and pulse rate can be applied to monitor the patient simultaneously with the fiber optic monitor described herein. Such a configuration can be useful for a variety of conditions, such as detecting and diagnosing apneic events in both infants and adults.

This invention is to be limited only by the following claims, which include all such embodiments and modifications when viewed in conjunction with the above specification and accompanying drawings.

What is claimed is:

1. A fiber optic, interferometric monitor for detecting vital functions in a patient, comprising:

an optical fiber interferometer that generates an optical signal responsive to acousto-mechanical signals generated by vital functions of said patient, including optical fiber means for defining two optical paths including a first optical path and a second optical path;

said first optical path including an optical fiber proximately situated to said patient so that said acousto-mechanical signals are coupled to said optical fiber, thereby modulating a physical parameter of said optical fiber responsive to said acousto-mechanical signals, an optical source coupled to supply optical radiation into an input end of said first and second optical paths, means for creating a serial train of fringes from the optical radiation emitted from an output end of said two optical paths;

a photo-detector arranged to sense an optical signal provided by time variations in said fringe train, said photo-detector providing a raw electrical signal responsive thereto;

a signal processor coupled to said optical detector to process said raw electrical signal to provide one or more processed output signals indicative of said vital functions; and an output system for said one or more processed signals.

2. The monitor of claim 1 wherein said modulated physical parameter comprises the length of said optical fiber, such that said acousto-mechanical signals modulate the length of said optical fiber.

3. The monitor of claim 1 wherein said output signals indicative of said vital functions include heartbeat, respiration, and movement.

4. The monitor of claim 3 wherein said signal processor comprises a digital signal processor for providing separate output signals indicative of heartbeat rate, respiration rate, and physical movement.

5. The monitor of claim 3 wherein said output signals include a combined signal indicative of heartbeat and respiration rates.

6. The monitor of claim 3 wherein said signal processor comprises means for generating an alarm responsive to at least one of said heartbeat, respiration, and physical movement.

7. The monitor of claim 1 further comprising a pad within which said optical fiber sensor is situated, said pad being positioned proximate to said patient.

8. The monitor of claim 7 wherein said pad has a mat configuration, and said patient rests on said mat.

9. The monitor of claim 7 wherein said pad has a garment configuration such that said patient wears said pad.

10. The monitor of claim 1 wherein said output system includes a transmission system that transmits at least one of said signals to a receiver situated remotely from said patient.

11. The monitor of claim 10 wherein said receiver includes a portable receiver unit and means for providing an alarm responsive to said at least one of said output signals.

12. The monitor of claim 1 further comprising a depolarizer for reducing polarization-induced signal fading.

13. The monitor of claim 1 wherein said fiber interferometer comprises a Sagnac interferometer configuration.

14. The monitor of claim 1 wherein said fiber interferometer comprises a Mach-Zehnder interferometer configuration.

15. The monitor of claim 1 wherein said fiber interferometer comprises a Fabry-Perot interferometer configuration.

16. The monitor of claim 1 wherein said fiber interferometer comprises a Michelson interferometer configuration.

17. The monitor of claim 1 further comprising one or more additional sensors arranged to monitor physical parameters in said patient.

18. The monitor of claim 17 wherein said one or more additional sensors are selected from a group comprising: a microphone, a camera, an oxygen sensor, a carbon dioxide sensor, a temperature sensor, an EKG monitor and a second fiber optic interferometer.

19. A method for detecting vital functions of a patient utilizing an optical fiber interferometer, comprising:

coupling optical radiation into a first end of a first optical path and a second optical path, said first optical path including a first section of optical fiber;

situating said first section of optical fiber proximate to said patient;

coupling acousto-mechanical signals indicative of vital signs generated by said patient into said first section of optical fiber to modulate a physical parameter of said optical fiber responsive to said acousto-mechanical signals;

creating a serial train of fringes from the optical radiation emitted from a second end of said two optical paths;

detecting time variations of said fringes and providing a time-varying electrical signal responsive thereto; and signal processing said time-varying electrical signal to provide one or more output signals indicative of said vital functions.

20. The method of claim 19 wherein said step of modulating a physical parameter comprises modulating the phase of said optical fiber.

21. The method of claim 19 wherein said signal processing step comprises providing output signals indicative of vital functions including heartbeat rate, respiration rate, and physical movement.

22. The method of claim 21 wherein said signal processing step comprises digitally processing said time-varying electrical signal to provide separate output signals indicative of heartbeat rate, respiration rate, and physical movement.

23. The method of claim 21 wherein said signal processing step comprises processing said time-varying electrical signal to provide a combined signal indicative of heartbeat and respiration rates.

24. The method of claim 21 wherein said signal processing step comprises processing said time-varying electrical signal to generate an alarm signal responsive to at least one of said heartbeat rate, respiration rate, and physical movement.

25. The method of claim 19 wherein said step of situating said first section of optical fiber proximate to said patient further comprises positioning said patient on a pad in a bed.

26. The method of claim 19 said step of situating said first section of optical fiber proximate to said patient further comprises wearing a garment including said first section of optical fiber.

27. The method of claim 19 further comprising the step of communicating said output signals.

28. The method of claim 27 wherein said step of communicating said signals further comprises transmitting said signal to a receiver positioned remotely from said patient.

29. The method of claim 19 further comprising the step of simultaneously monitoring one or more physical parameters of said patient with a second sensor.

30. The method of claim 29 comprising the step of monitoring the oxygen level in said patient.

31. A fiber optic, interferometric infant monitor for detecting vital functions in an infant within a crib, comprising:

a pad having an optical fiber situated therein, said pad arranged within said crib proximate to said infant so that acousto-mechanical signals generated by said infant are coupled into said optical fiber;

a fiber interferometer that generates an optical signal responsive to acousto-mechanical signals generated by vital functions of said infant, including optical fiber means for defining two optical paths including a first optical path and a second optical path, said first optical path including said optical fiber situated within said pad;

an optical source coupled to supply optical radiation into an input end of said first and second optical paths, an optical system for creating a serial train of fringes from the optical radiation emitted from an output ends of said two optical paths; and a photo-detector arranged to sense an optical signal provided by time variations in said fringe train, said photo-detector providing a raw electrical signal responsive thereto;

a signal processor coupled to said optical detector to process said raw electrical signal to provide one or more processed output signals indicative of heartbeat rate, respiration rate, and physical movement; and an output system that communicates said one or more output signals.

32. The monitor of claim 31 further comprising an audio system that detects and transmits sounds, including a microphone arranged to detect sounds generated by the infant.

33. The monitor of claim 31 wherein said pad has a mat configuration, and said infant rests on said mat.

34. The monitor of claim 31 wherein said output system includes a transmission system that transmits at least one of said signals to a receiver situated remotely from said infant.

35. The monitor of claim 34 wherein said receiver includes a portable receiver and means for providing an alarm responsive to said at least one of said output signals.

36. The monitor of claim 34 wherein said receiver includes a speaker to provide sounds generated by the infant.

37. The monitor of claim 31 wherein said output signals include a combined signal indicative of heartbeat and respiration rates.

38. The monitor of claim 31 wherein said signal processor comprises means for generating an alarm responsive to at least one of said heartbeat rate, respiration rate, and physical movement.

39. The monitor of claim 31 wherein said signal processor comprises a digital signal processor for providing separate output signals indicative of heartbeat rate, respiration rate, and physical movement.

40. The monitor of claim 31 wherein said pad has a garment configuration such that said infant wears said pad.

41. The monitor of claim 31 further comprising a means for reducing polarization-induced signal fading.

42. The monitor of claim 31 wherein said fiber interferometer comprises a Sagnac interferometer configuration.

43. The monitor of claim 31 wherein said fiber interferometer comprises a Mach-Zehnder interferometer configuration.

44. The monitor of claim 31 wherein said fiber interferometer comprises a Fabry-Perot interferometer configuration.

45. The monitor of claim 31 wherein said fiber interferometer comprises a Michelson interferometer configuration.

46. The monitor of claim 31, further comprising one or more additional sensors arranged to monitor physical parameters in said patient.

47. The monitor of claim 46 wherein said one or more additional sensors are selected from a group comprising: a microphone, a camera, an oxygen sensor, a carbon dioxide sensor, a temperature sensor an EKG monitor and a second (or more) fiber optic interferometer.

* * * * *

UNITED STATES PATENT AND TRADEMARK OFFICE
CERTIFICATE OF CORRECTION

PATENT NO.     : 6,498,652 B1
DATED          : December 24, 2002
INVENTOR(S)    : Varshneya et al.

It is certified that error appears in the above-identified patent and that said Letters Patent is hereby corrected as shown below:

<u>Title page,</u>
Insert the following:

-- [73] Assignee: Deepak Varshneya, Del Mar, CA (US). --

-- [74] *Attorney, Agent, or Firm* - Watts, Hoffmann, Fisher & Heinke, Co., L.P.A. --

Signed and Sealed this

First Day of April, 2003

JAMES E. ROGAN
*Director of the United States Patent and Trademark Office*